US008420605B2

(12) United States Patent
Ulijn et al.

(10) Patent No.: US 8,420,605 B2
(45) Date of Patent: Apr. 16, 2013

(54) HYDROGEL COMPOSITIONS

(75) Inventors: Rein Vincent Ulijn, Rainhill (GB); Vineetha Jayawarna, Cheadle Hulme (GB); Andrew Smith, Leeds (GB); Julie Elizabeth Gough, Ramsbottom (GB)

(73) Assignee: The University of Strathclyde, Glasgow (GB)

( * ) Notice: Subject to any disclaimer, the term of this patent is extended or adjusted under 35 U.S.C. 154(b) by 1027 days.

(21) Appl. No.: 11/470,962

(22) Filed: Sep. 7, 2006

(65) Prior Publication Data
US 2007/0099840 A1 May 3, 2007

Related U.S. Application Data

(60) Provisional application No. 60/714,583, filed on Sep. 7, 2005.

(51) Int. Cl.
*A61K 38/08* (2006.01)
*A61K 38/06* (2006.01)
*A61K 38/07* (2006.01)
*A61K 38/05* (2006.01)

(52) U.S. Cl.
USPC .................. 514/21.8; 514/21.9; 514/21.92

(58) Field of Classification Search .................. None
See application file for complete search history.

(56) References Cited

U.S. PATENT DOCUMENTS

| 7,491,699 B2 * | 2/2009 | Reches et al. ................ 514/12 |
| 2003/0022405 A1 | 1/2003 | Song et al. |
| 2004/0265951 A1 | 12/2004 | Messersmith et al. |
| 2007/0099840 A1 * | 5/2007 | Ulijn et al. .................. 514/17 |
| 2007/0224273 A1 * | 9/2007 | Xu et al. .................... 424/488 |
| 2009/0175785 A1 * | 7/2009 | Gazit et al. ................. 424/1.29 |
| 2009/0263429 A1 | 10/2009 | Ulijn et al. |

FOREIGN PATENT DOCUMENTS

| EP | 0278787 A1 | 8/1988 |
| WO | WO98/08492 * | 3/1998 |
| WO | 2001/074928 A1 | 10/2001 |
| WO | WO 2006/037113 | 4/2006 |
| WO | 2007/012876 A1 | 2/2007 |
| WO | WO 2007/043048 | 4/2007 |

OTHER PUBLICATIONS

Xing et al. Hydrophobic Interaction and Hydrogen Bonding Cooperatively Confer a Vancomycin Hydrogel: A Potential Candidate for Biomaterials. JACS Communications. 2002, 124, pp. 14846-14847.*
Reches et al. Self-Assembly of Peptide Nanotubes and Amyloid-like Structures by Charged-Termini-Capped Diphenylalanine Peptide Analogues. Israel Journal of Chemistry. Sep. 1, 2005. vol. 45, Issue 3, pp. 363-371.*
Silva et al. Selective Differentiation of Neural Progenitor Cells by High-Epitope Density Nanofibers. Science 2004, vol. 303, pp. 1352-1355.*
Jayawarna et al. Nanostructured Hydrogels for Three-Dimensional Cell Culture Through Self-Assembly of Fluorenylmethoxycarbonyl Dipeptides. Adv. Mater. 2006. vol. 18, pp. 611-614.*
Jayawarna et al. Three-dimensional cell culture of chondrocytes on modified di-phenylalanine scaffolds. Biochemical Society Transactions. 2007. vol. 35, part 3, pp. 535-537.*
Yang et al. Enzymatic Hydrogelation of Small Molecules. Accounts of Chemical Research. Published on the Web Jan. 19, 2008. vol. 1, No. 2, pp. 315-326.*
Lutolf MP et al., "Synthetic biomaterials as instructive extracellular microenvironments for morphogenesis in tissue engineering," Nature Biotechnology, vol. 23, No. 1, Jan. 2005, pp. 47-55.
Yang Z et al., "Self-assembly of small molecules affords multifunctional supramolecular hydrogels for topically treating simulated uranium wounds," Chem. Commun., 2005, 4414-4416.
Schneider JP et al., "Responsive hydrogels from the intramolecular folding and self-assembly of a designed peptide," J. Am. Chem. Soc. 2002, 124, 15030-15037.
Yang Z et al., "A simple visual assay based on small molecule hydrogels for detecting inhibitors of enzymes," Chem. Commun., 2004, 2424-2425.
Yang Z et al., "Small molecule hydrogels based on a class of antiinflammatory agents," Chem. Commun., 2004, 208-209.
Yang Z et al., "Enzymatic formation of supramolecular hydrogels," Adv. Mater. 2004, 16, No. 16, Aug. 18, pp. 1440-1444.
Yang Z et al., "Supramolecular hydrogels respond to ligand-receptor interaction," J. Am. Chem. Soc. 2003, 125, 13680-13681.
Alvarex-Macarie E., Baratti J., "Short chain flavour ester synthesis by a new esterase from *Bacillus lichenformis*", Journal of Molecular Catalysis B, 2000, 10, pp. 377-383.
Hailing P.J., et al., "Understanding enzyme action on immobilising substrates", Current Opinion in Biotechnology, 2005,16, 385-392.
Hu-Bi Yuang et al., "Rational Design of trangluminase substrate peptides for rapid enzymatic formation of hydrogels", Journal of the American chemical society, 2003, vol. 125, No. 47, 14298-14299.
Kuhl P. et al., H-D, "Model Studies on Protease-Catalysed Peptide Synthesis Using 9-Fluorenylmethoxycarbonyl Protected Amino Acid Derivatives", Monatshefte fuer Chemie, 1992, 123, 1015-1022.
Ivanov Vailo, et al., "Thermodynamics of enzymatic synthesis of solid-phase peptides", Tetrahedron, vol. 49, 1993, 2307-2316.

(Continued)

*Primary Examiner* — Marcela M Cordero Garcia
(74) *Attorney, Agent, or Firm* — Nixon & Vanderhye P.C.

(57) ABSTRACT

Hydrogel compositions comprise an aqueous dispersion phase and a plurality of peptides, or derivatives, or analogues thereof. Each peptide comprises at least two amino acid residues and an aromatic stacking ligand and the hydrogel is formed by self-assembly of said peptides in said aqueous dispersion medium. The aqueous dispersion phase is physiologically acceptable and may have a pH of 6 to 8, as may the hydrogel itself. The hydrogel may be used for cell culture or for treatment of medical conditions characterized by tissue loss/damage.

25 Claims, 6 Drawing Sheets
(3 of 6 Drawing Sheet(s) Filed in Color)

OTHER PUBLICATIONS

Petkov D. et al., "Enzyme Peptide Synthesis by an interative procedure in a nucleophile pool", Tetrahedron letters, vol. 25, No. 34, 1984, pp. 3751-3754.

Plunkett K., el al. "Chymotrypsin responsive hydrogel: Application of a disulfide exchange protocol for the preparation of methylacrylamide containing peptides", Biomacromolecules, 2005, vol. 6, No. 2, pp. 632-637.

Sakina et al., "Thermocatalysed Synthesis of Peptide amides Chemical and Pharmaceutical Bulletin," vol. 36 No. 11, 1988, pp. 4345-4354.

Schuster M. et al, Chymotrypsin-catalyzed peptide synthesis in ice: use of unprotected amino acids as acyl acceptors, Tetrahedron letters, vol. 34, No. 36, 1993, pp. 5701-5702.

Toledano, Ulijin R.J, et al, "Enzyme-Triggered Self-Assembly of Peptide Hydrogels via Reversed Hydrolysis" Journal of the American Chemical Society, 2006, 128, 1070-1071.

Wilson S.A, et al., "Peptide Synthesis with Proteinase from the Extremely Thermophilic Organism Thermus Rt41A", Biotechnology and Bioengineering, 1994, vol. 44, p. 337-346.

Office Action dated Oct. 5, 2011 issued in connection with U.S. Appl. No. 11/991,768.

Office Action dated Jul. 9, 2012 issued in connection with U.S. Appl. No. 11/991,768.

Wayne and Fruton, "Thermolysin-catalyzed peptide bond synthesis", Proc. Natl. Acad. Sci. USA 80:3241-3244 (1983).

Doeze et al, "Profiling Primary Protease Specificity by Peptide Synthesis on a Solid Support", Angew. Chem. Int. Ed. 43:3138-3141 (2004).

Ulijn et al, "Solvent Selection for Solid-To-Solid Synthesis", Biotechnology and Bioengineering 80(5):501-515 (2002).

Communication dated Nov. 30, 2010 issued in connection with EP 06779343.0.

International Search Report dated Jun. 26, 2007 issued in connection with PCT/GB2006/003325, filed Sep. 7, 2006.

Zhang et al, "Supramolecular Hydrogels Respond to Ligand-Receptor Interaction", J. Am. Chem. Soc. 125:13680-13681 (2003).

* cited by examiner

Figure: 10
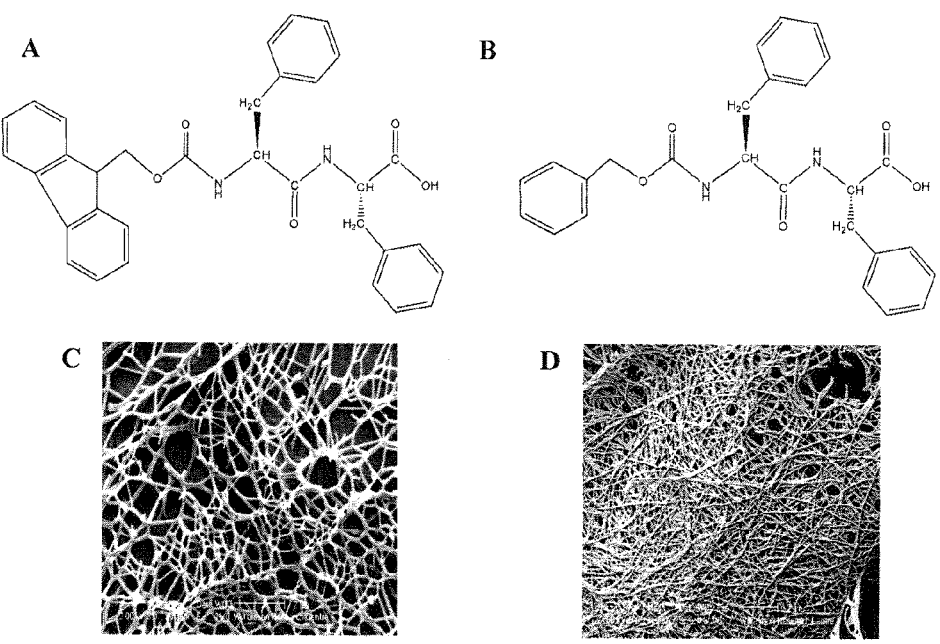

HYDROGEL COMPOSITIONS

FIELD OF INVENTION

The present invention relates to hydrogels and particularly, although not exclusively, to hydrogels formed from self-assembling peptides. More specifically, the invention relates to the use of such hydrogels as cell supporting media and cell scaffolds, and to methods of preparing such scaffolds. The invention further extends to uses of the cell supporting media and scaffolds, for example, in medicine, including methods of treatment.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Pre-designed self-assembling scaffolds are highly advantageous in areas such as tissue regeneration/engineering, 3D cell culture, in vitro toxicity testing, understanding cell/extracellular matrix interactions, controlled stem cell differentiation, studies of mechanical loading effects on cells, and the study of metastasis models. In particular, developments in the use of self-assembling peptides provide potential for the use of such novel bionanomaterials in tissue engineering. The various properties of the amino acids in peptides, their biological compatibility, and the inherent properties of their bonded structure make peptides a very powerful building block for the fabrication of self-assembling scaffolds.

Advances have been made in creating synthetic mimics of the Extracellular Matrix for in vivo and in vitro applications. Some researchers have described the use of peptides with alternating charged, hydrophobic and hydrophilic amino acids to culture nerve cells, endothelial cells and chondrocytes. Other researchers have demonstrated the use of synthetic amphiphile peptide-containing molecules that can self-assemble into fibrous scaffolds that support cell growth and stem cell differentiation. These successes illustrate that man-made hydrogels could be useful for forming scaffold materials for 3D cell culture and tissue engineering applications.

Xu et. al. (J. Am. Chem. Soc. 2003, 125, 13680) described that Fmoc (fluorenylmethoxycarbonyl) protected di-peptides could form fibrous scaffolds at low pH values by taking advantage of π-stacking of the highly conjugated Fmoc group. Examples of Fmoc-dipeptides disclosed by Xu et al as being capable of forming such gels are Fmoc-D-Ala-D-Ala (3), Fmoc-L-Ala-L-Ala (3), Fmoc-Gly-Gly (3), Fmoc-Gly-D-Ala (5) and Fmoc-Gly-L-SER (5), the numbers in parentheses being the pH value for gelation. Fmoc is widely used as a protecting group in peptide chemistry and when coupled to amino acids, is known to have anti-inflammatory properties, as demonstrated in animal studies. The Fmoc group acts as a "stacking ligand", thought to offer order and directionality to the self-assembly process. However, Xu et al carried out all of their investigations at substantially acidic pH's (i.e. pH 3-5), and did not investigate whether the compounds could be used in biologically acceptable (ie. physiologically agreeable) conditions.

Although considerable efforts have been made towards understanding the behaviour of hydrogel scaffolds, the present knowledge on the subject is very limited as much of these studies have been based on trial and error. Furthermore, little has been reported on the rules that govern self-assembly or the functioning of the peptide scaffolds under different conditions. For use of such scaffolds in biological or medical conditions, it is important to understand the scaffold behaviour, especially under environmental conditions similar to those experienced in vivo. Furthermore, ultimately, researchers would like to design scaffolds rationally for use in vivo.

Furthermore, up until now, it has not been possible to make scaffolds from small molecule building blocks that are: (i) stable under tissue culture conditions (i.e. high ionic strength, and pH 7); (ii) of similar dimensions to fibrous components of the extracellular matrix; (iii) capable of supporting cell culture in 3D; (iv) optically transparent; and (v) capable of liquid to gel transitions on demand by biocompatible means.

Therefore, it is an aim of the present invention to obviate or mitigate one or more of the problems of the prior art, whether identified herein or elsewhere, and to provide improved hydrogels, which may be used in vitro or in vivo to support cell cultures, and to provide methods of treatment, which use such hydrogels.

BRIEF DESCRIPTION OF THE FIGURES

Exemplary embodiments are illustrated in referenced figures. It is intended that the embodiments and figures disclosed herein are to be considered illustrative rather than restrictive.

The file of this patent contains at least one drawing executed in color. Copies of this patent with color drawing(s) will be provided by the patent and Trademark Office upon request and payment of the necessary fee.

FIG. 10 illustrates a comparison of Fmoc and CBz as aromatic stacking ligands in accordance with various embodiments of the present invention. A: the structure of Fmoc-Phe-Phe-OH; B: the structure of Cbz-Phe-Phe-OH; C: Cyro-SEM image of Fmoc-Phe-Phe-OH; D: Cryo-SEM image of Cbz-Phe-Phe-OH.

DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. One skilled in the art will recognize many methods and materials similar or equivalent to those described herein, which could be used in the practice of the present invention. Indeed, the present invention is in no way limited to the methods and materials described.

The inventors of the present invention investigated the design and preparation of hydrogels consisting of self-assembling peptides, as they believed that these could be used to form a scaffold that mimics the extracellular matrix (ECM) of certain tissues. The inventors wanted to investigate if these hydrogels would be capable of supporting individual cells and cell cultures under biologically acceptable conditions, i.e. stable under in vivo tissue culture conditions of high ionic strength, and a neutral pH. As a model cell culture, the inventors focussed their research on supporting cultures of chondrocytes (cartilage cells) on the hydrogel scaffold.

Figure 4:
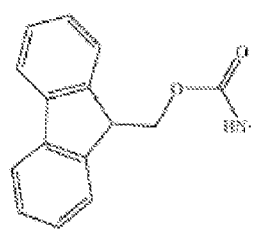
FIG. 4 shows the structure of Fmoc used in accordance with various embodiments of the present the invention.

The inventors therefore produced a dipeptide as discussed in Example 1, which consists of the amino acid, Phenylalanine (Phe), the structure of which will be known to the skilled technician. The dipeptide was attached to, and protected with, Fmoc (fluorenylmethoxycarbonyl), the structure of which is shown in FIG. 4, and will also be known to the skilled technician. The inventors wished to investigate whether or not an Fmoc cap could be useful in the formation of a hydrogel scaffold. Hence, the peptide produced was Fmoc-Phe-Phe.

The inventors attempted to prepare self-assembled hydrogels by suspending the Fmoc-Phe-Phe dipeptide in purified water, and then varying the pH. The inventors were surprised to find that the Fmoc-Phe-Phe (diphenylalanine) was able to self-assemble into a hydrogel in a physiological buffer under biologically acceptable conditions (pH=7.0). To date, this had not been possible. The inventors also investigated the stability of the hydrogel by adding the amino acid lysine thereto, and again found that the hydrogel (Phe-Phe+Lysine) was stable at pH 7. Finally, the inventors investigated the stability of the hydrogel by adding a further dipeptide, Fmoc-Gly-Gly, to the mixture, and again found that the hydrogel (formed from a mixture of Phe-Phe+Gly-Gly) formed was stable at pH 7.

Surprised to find that these dipeptides and mixtures were able to produce stable hydrogels under physiological conditions, the inventors decided to carry out further experiments. They also found that the hydrogels formed by the self-assembled peptides as described herein are surprisingly adapted to support cell cultures therein. Following on from the promising results produced with Fmoc-Phe-Phe dipeptides and mixtures thereof, the inventors wanted to investigate further how the design of the self-assembling peptides could be modified to produce other stable hydrogels under physiological conditions. The inventors therefore produced four tripeptides each of which consisted of Fmoc-X-Phe-Phe, where X=Alanine, Valine, Leucine, Phenylalanine. In addition, the inventors also made the tripeptide: Fmoc-Leu-Leu-Leu The inventors were surprised to see that each of these five tripeptides formed stable hydrogels, and were also able to support cell cultures.

Hence, in summary, the inventors have surprisingly demonstrated that the hydrogels formed from self-assembling peptides are:- (i) stable under biologically acceptable, tissue culture conditions; (ii) are of similar dimensions to fibrous components of the extracellular matrix (i.e. nano-sized fibres); and (iii) are capable of supporting cell culture in both 2D and in 3D. Hence, advantageously, the inventors believe that the hydrogels formed by such self-assembling Fmoc-dipeptides may be used in a wide range of medical applications, for example, in tissue engineering and regeneration scenarios, and in methods of treatment.

In its broadest, first aspect the present invention provides a hydrogel composition comprising an aqueous dispersion phase and a plurality of peptides, or derivatives, or analogues thereof, wherein each peptide comprises at least two amino acid residues and an aromatic stacking ligand, and wherein the hydrogel is formed by self-assembly of said peptides in said aqueous dispersion medium.

Preferred embodiments of hydrogel composition in accordance with the invention are formulated with a physiologically acceptable aqueous dispersion phase, preferably having a pH of 6 to 8. The hydrogel composition itself may have a pH of 6 to 8.

Preferred embodiments of hydrogel compositions in accordance with the invention are disclosed below in conjunction with proposed uses of the compositions.

The invention is able to provide hydrogels in the form of nanofibrous dense networks that are stable under physiological conditions. The hydrogels are comprised of di- or higher-peptides modified with aromatic stacking ligands and are stabilised by a combination of pi-pi interactions, hydrogen bonding and/or other non-covalent interactions (such as electrostatics). The gels have uses in maintaining and/or directing cell phenotype and cell behaviour such as motility, morphology, proliferation rate, adhesion, differentiation, or matrix production.

Furthermore, advantageously, by choosing specific amino acid residues, which make up the plurality of peptides, it is possible to vary the structural and functional properties of the hydrogel formed. Therefore, the peptides and hence the hydrogel may be specifically 'tailored', depending on the final use of the hydrogel.

According to a second aspect of the present invention, there is provided a method of treating an individual suffering from a medical condition characterised by tissue loss/damage, the method comprising providing at a treatment site of an individual in need of such treatment, a hydrogel comprised of gel-forming peptides, or derivatives, or analogues thereof, wherein each peptide comprises at least two amino acid residues and an aromatic stacking ligand.

The inventors have surprisingly found that the use of such peptides to form a hydrogel at the treatment site enables the formation of a hydrogel scaffold structure, which is adapted to support cell growth. The inventors observed that the cells are able to infiltrate the hydrogel at the treatment site, thereby forming a 3D cell culture. This cell culture therefore can replace and/or repair the tissue lost or damaged at the treatment site.

By the term "hydrogel", we mean a gel in which water is the major dispersion medium. Preferably, the water disperses the components of the hydrogel, ie. the peptides, derivatives or analogues thereof. Preferably, the hydrogel comprises at least 80% (w/w) water, more preferably, at least 85% (w/w) water, and more preferably, at least 90% (w/w), even more preferably, at least 95% (w/w) water.

The self-assembling subunits of the hydrogel (ie. the gel-forming peptides, derivatives or analogues thereof) may have a molecular weight of between 100 and 20,000 Da, more preferably, between 200 and 15,000 Da, and even preferably, between 300 and 12,000 Da.

In one embodiment, the hydrogel may be provided as a liquid precursor composition, which may then be induced in situ to form the hydrogel. Hence, the hydrogel may be prepared in situ in the treatment site. In another embodiment, the hydrogel may be formed remote from the treatment site, for example, in a mould, which may then be administered to the treatment site. The choice of how to administer the hydrogel to the treatment site will depend on the medical condition being treated. In either case, the hydrogel may be used as a scaffold structure to support cells therein, to thereby repair the site of tissue loss or damage.

Hence, the inventors believe that the method according to the second aspect, may be used in wide variety of different medical treatments for treating a medical condition characterised by tissue loss/damage. Examples of conditions that may be treated include the treatment of wounds, and related injuries, and tissue degenerative disorders. For example, the wound may be chronic, and may be abrasive, for example, burns. The wound may be formed by pressure, such as decubitus ulcers, and bed-sores. The wound may be acute, and may be penetrative such as a cut, or a stab wound, or the result of a crush to the body of the individual requiring treatment.

Tissue degenerative disorders that may be treated using the method include neurodegenerative, intervertebral disc disorders, cartilage or bone degeneration such as osteoarthritis, osteoporosis, liver degenerative disorders, kidney degenerative disorders, muscle atrophy.

Preferably, and advantageously, the peptides, or derivatives, or analogues thereof used in the method according to the invention may be induced to form a hydrogel. The hydrogel is preferably optically transparent, which is an advantage for medical practitioners to clearly see the treatment site when using the hydrogel in the method. It is preferred that the hydrogel is provided in a physiologically acceptable excipient (or aqueous dispersion medium). By the term "physiologically acceptable excipient", we mean any suitable solution, which is capable of conferring biologically acceptable conditions on the peptides such that they self-assemble (i.e. with each other) resulting in gelation to form the hydrogel. Examples of suitable excipients will be known to the skilled technician, and may comprise a physiological buffer, such as saline. Preferably, the excipient is provided at a biologically acceptable pH.

Hence, the inventors have demonstrated for the first time that peptides, derivatives or analogues thereof may be contained within a physiologically acceptable excipient, such that the peptides which are attached to an aromatic stacking ligand, self-assemble to form the hydrogel. Hence, preferably, the excipient confers biologically acceptable conditions on the peptides, derivatives or analogues thereof, such that interactions between the stacking ligands cause the peptides, derivatives or analogues thereof to form a hydrogel either in the treatment site, or prior to administration thereto.

Previous researchers have only demonstrated preparation of hydrogels under non-physiological (i.e. biologically unacceptable) conditions, for example, where the pH is substantially low and therefore acidic. Hence, to date, it has not been possible to form hydrogels at biologically acceptable pH's. Hence, the prior art does not contemplate the use of such hydrogels in medical contexts, as it will be appreciated that acidic conditions will be wholly unsuitable for biological applications of the hydrogel used in the method according to the invention. Therefore, the inventors believe that use of the hydrogel in the method of the invention is a significant advance over current technology.

It is preferred that the biologically acceptable excipient is at a pH of between 5 and 9, more preferably between 6 and 8, even more preferably, between about 6.5 and about 7.5. It will be appreciated that the pH of most cells is about 7.4. Hence, a most preferred excipient has a pH of between about 7 and about 7.5. It will be appreciated that such pHs are referred to as being biologically acceptable conditions.

By the term "biologically acceptable conditions", we mean the hydrogel used in the method of the invention is substantially stable under in vivo conditions, i.e. conditions of pH, ionic strength and temperature, which would be found in vivo. The inventors envisage primarily using the method according to the invention, and hence, the hydrogel, to treat disorders charaterised by tissue damage/loss in mammals and, in particular, man. Therefore, it is preferred that the hydrogel is formed and is stable under biologically acceptable conditions in mammals, and preferably, in man.

Hence, the inventors investigated the stability of the hydrogel at a biologically acceptable pH. Since the inventors envisage primarily using the hydrogel in mammals, they considered a biologically acceptable pH at which the hydrogel should be stable to be between about 5.0 to about 9.0. The inventors believe that the treatment site in the disorders being treated would be within this pH range. However, it is preferred that the hydrogel is formed at a pH of between about 6.0 to about 8.0. As described herein, the method may be used to treat wounds. In chronic wounds, the pH may be between a 6.0 and 8.0. Hence, when treating chronic wounds, it is preferred that the hydrogel is stable between a pH of about 6.0 and 8.0.

However, when treating other disorders, the hydrogel may be formed at a pH of between about 6.5 to about 7.5. It is more preferred that the hydrogel is formed at a pH of between about 6.7 to about 7.3, and still more preferably, between about 6.9 to about 7.1. It will be appreciated that it is most preferred that the hydrogel is formed at about pH 7.0. It is preferred that the hydrogel is substantially stable at these biologically acceptable pH's.

The inventors also investigated the stability of the hydrogel under biologically acceptable ionic conditions. The inventors believe that the treatment site of the individual being treated would be at a high ionic strength. Hence, it is preferred that the hydrogel is formed in conditions of substantially high ionic strength. Hence, the ionic strength may be between about 0.01M to about 1M, preferably, between about 0.05M to about 0.5M, more preferably, between about 0.1 to about 0.2, and even more preferably, between about 0.12M and about 0.17M.

Furthermore, the inventors investigated the stability of the hydrogel at biologically acceptable temperatures. Since the inventors envisage primarily using the hydrogel in the method to treat mammals and in particular man, they considered biologically acceptable temperatures to be between about 32° C. to about 40° C. Hence, it is preferred that the hydrogel used in the method is substantially liquid at temperatures above about 40° C.

The inventors were surprised to find that it was possible to tightly control the gelation of the hydrogel at temperatures below 40° C. In fact, they found that the critical gelation temperature for the hydrogel was at about body temperature (i.e. 37° C. and below), and that the gel liquifies at temperatures greater than body temperature. This is a major advantage for use of the hydrogel in medicine, as it is therefore possible to induce transition of the peptides from liquid form (sol) to hydrogel (gel) on demand when in situ in the treatment site. Hence, preferably, the hydrogel used in the method is formed below about 40° C., more preferably below about 39° C., and even more preferably, below about 38° C. Therefore, preferably, the hydrogel is formed at a temperature of between about 36° C. to about 38° C., and most preferably, at about 37° C.

However, it should be appreciated that in chronic wounds, and also in surface organs (such as the skin, the eye etc.) the temperature may be a few degrees lower, for example, about 32° C. to 34° C. Hence, in embodiments of the method where the composition is used to treat chronic wounds or surface organs, it is preferred that the hydrogel forms at a temperature of between about 32° C. to 34° C.

Therefore, in preferred embodiments of the invention, it is preferred that the hydrogel forms at a pH of between about 6.8 to about 7.5, a high ionic strength, and at a temperature of between about 32° C. to about 38° C.

It will be appreciated that the hydrogel used in the method according to the second aspect of the invention may comprise a plurality of identical peptides, or a plurality of peptides that are different. Nevertheless, in either case, each peptide in the hydrogel comprises at least two amino acid residues or derivatives or analogues thereof attached to an aromatic stacking ligand, such that interactions therebetween causes the hydrogel to form. The inventors have found that surprisingly, at least two amino acid residues are required in each peptide. This is because if a peptide comprises less than two amino acid residues, it results in either no hydrogel forming at all, or an inferior hydrogel being formed, at biologically acceptable conditions.

Peptides of the hydrogel used in the method may comprise at least three, four, five, six, or more amino acids or derivatives or analogues thereof, or any combination thereof. However, it is preferred that the peptides may comprise less than 10 amino acids or derivatives or analogues thereof, more preferably less than 8 amino acids or derivatives or analogues thereof, and even more preferably, less than 6 amino acids or derivatives or analogues thereof. Hence, peptides of the hydrogel may comprise at least 2 amino acids and less than 7 amino acids, or derivatives or analogues thereof. For example, the hydrogel used in the method according to the invention may comprise a dipeptide, a tripeptide, a tetrapeptide, a pentapeptide, hexapeptide, and/or a heptapeptide etc., or derivatives or analogues thereof, or any combination thereof.

The hydrogel used in the method according to the invention may comprise a number of identical peptides, a number of peptides that are different from each other, or any combination thereof. Therefore, in one embodiment, the hydrogel may comprise all dipeptides, or all tripeptides, or all tetrapeptides etc. In another embodiment, the hydrogel may comprise a combination of dipeptides and tripeptides, or a combination or tripeptides and tetrapeptides. In yet another embodiment, the hydrogel may comprise a combination of dipeptides, tripeptides, and tetrapeptides, and so on.

Advantageously, smaller peptides such as dipeptides and tripeptides are conveniently small molecules compared to longer peptides (greater than 10 amino acid residues), and are therefore relatively simple and cheap to synthesise. Moreover, due to their small size, dipeptides and tripeptides also exhibit excellent stacking characteristics to thereby form the scaffold under the biologically acceptable conditions.

Figure 1:
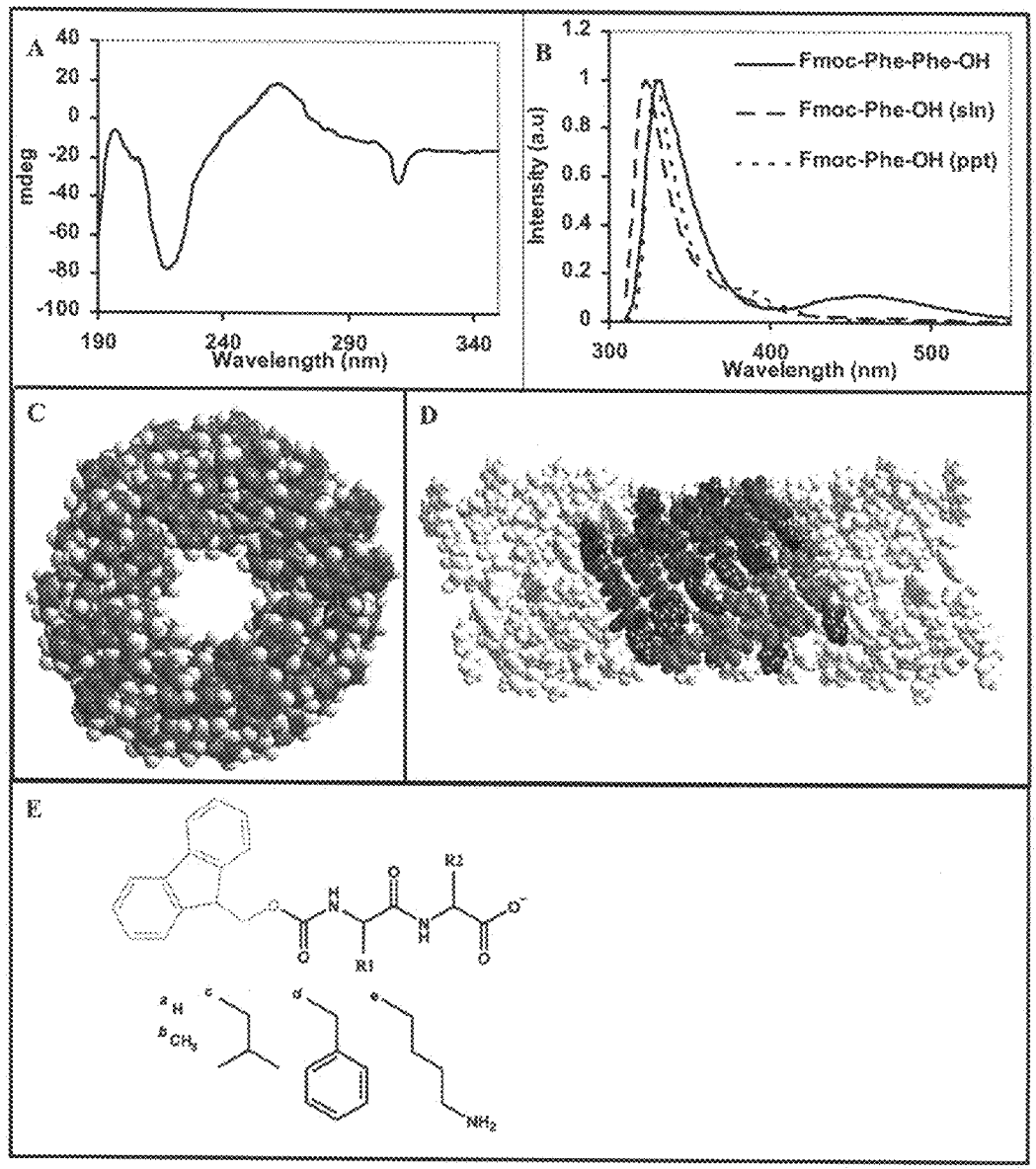
FIG. 1 depicts spectroscopic data and putative structures in relation to hydrogels comprised of Fmoc-Phe-Phe in accordance with various embodiments of the present invention.

The inventors have found that the physical properties of the hydrogel formed by the hydrogel under biologically acceptable conditions in the treatment site may be altered or 'tuned' by choosing different combinations of amino acid residues in the plurality of peptides. As described in the Examples, the characteristics of the resultant hydrogels may then be analysed by Circular Dichroism, and imaged by a CryoScanning Electron Microscope, examples of which are shown in FIG. 1.

Hence, the amino acids in the plurality of peptides in the hydrogel used in the method according to the second aspect of the invention may be selected from the repertoire of twenty amino acids commonly found in proteins, or any non-naturally occurring amino acids, and the specific amino acids chosen will depend on the final use of the hydrogel, and the condition being treated. For example, the hydrogel may comprise an acidic amino acid, such as aspartic acid, glutamic acid, asparagines, or glutamine; or a basic amino acid, such as histidine, lysine, or arginine. Variation of such amino acids in the peptide will influence the pH of the peptide, and hence, the hydrogel formed. The pH of the hydrogel may therefore be varied depending on the pH of the treatment site.

The gel-forming peptides may comprise a dipeptide and the aromatic stacking ligand. Alternatively the gel-forming peptides may comprise a tripeptide and the aromatic stacking ligand.

The hydrogel may comprise a hydrophobic amino acid, such as alanine, cysteine, isoleucine, leucine, methionine, phenylalanine, proline, tryptophan, valine or tyrosine; or a hydrophilic amino acid, such as arginine, asparagine, aspartate, glutamine, glutamate, histidine, lysine, serine, or threonine.

The inventors found that if the peptide comprises two consecutive or adjacent phenylalanine residues, that stable and effective hydrogels are formed. Hence, preferably the peptide comprises at least two consecutive phenylalanine residues.

Therefore, a preferred peptide used in accordance with the invention is Phe-Phe, which is described in the Example. The inventors carried out further investigations as described in Example 2, and found that introduction of a further amino acid immediately before the Phe-Phe also formed stable hydrogels. Hence, the inventors produced four tripeptides each of which consisted of Fmoc-X-Phe-Phe, where X=Ala, Val, Leu, Phe. Hence, further preferred peptides include Ala-Val-Phe; Val-Phe-Phe; Leu-Phe-Phe; and Phe-Phe-Phe.

In addition, the inventors also made the tripeptide : Fmoc-Leu-Leu-Leu, which also formed stable hydrogels and is also considered a preferred peptide for use in the method according to the invention.

The hydrogel may comprise first and second peptides each incorporating a dipeptide and an aromatic stacking ligand. The dipeptide of the first peptide may be Phe-Phe and the dipeptide of the second peptide may be Gly-Gly.

The inventors investigated modifying the peptides in the hydrogel used in the method according to the invention by choosing specific amino acids and combinations thereof. They found that it was possible to tailor the structural and functional characteristics of the resultant hydrogel formed under biologically acceptable conditions. For example, at least one peptide in the hydrogel may comprise at least one amino acid, which is adapted to initiate or promote cell-cell adhesion. For example, the or each peptide may comprise at least one tryptophan residue, which may mimick cadherin-mediated cell-cell interactions. It is preferred that the tryptophan residue is the amino acid residue distal from the aromatic stacking ligand.

As discussed herein, the inventors have surprisingly found that the hydrogel used in the method according to the invention is formed due to the presence of the aromatic stacking ligand (A.S.L.). Hence, the peptide may preferably have the following structure: A.S.L.-$AA_1$-$AA_2$-X, where A.S.L. denotes the Aromatic Stacking Ligand, where $AA_n$ denotes amino acid residues in the peptide (n= the number of the amino acid residue, e.g. n =1 or 2), and where X is a amino acid residue selected from the group consisting of Phe, Leu, IKVAV (SEQ. ID. NO. 3), RGD and KPV.

At least one peptide in the hydrogel may comprise an Arginine-Glycine-Aspartate (RGD) peptide motif. The inventors believe that incorporation of the RGD motif (which is a known cell adhesive) will improve the efficacy of the hydrogel to adhere to cells, which would be useful in the method of the second aspect as cell proliferation in the hydrogel will be promoted. Hence, the or each peptide may preferably have the following structure: A.S.L.-$AA_1$-$AA_2$-RGD, where A.S.L. denotes the Aromatic Stacking Ligand, where $AA_n$ denotes amino acid residues in the peptide, and where RGD denotes the RGD motif. It will be appreciated that the above structure is a pentapeptide.

At least one peptide in the hydrogel may comprise an Isoleucine-Lysine-Valine-Alanine-Valine (IKVAV: SEQ. ID. NO. 3) peptide motif. The inventors believe that incorporation of the IKVAV motif (which is known to directionally guide nerve cells) will improve the efficacy of the hydrogel to guide nerve cells, which would be useful in the method of the second aspect when involving nerve growth, wound repair or nerve tissue regeneration. Hence, the or each peptide may preferably have the following structure: A.S.L.-$AA_1$-$AA_2$-(SEQ. ID. NO. 3), where A.S.L. denotes the Aromatic Stacking Ligand, where $AA_n$ denotes amino acid residues in the peptide, and where IKVAV denotes the IKVAV motif (SEQ. ID. NO. 3). It will be appreciated that the above structure is a heptapeptide.

At least one peptide in the hydrogel may comprise Lysine-Proline-Valine (KPV) motif. The inventors believe that incorporation of the KPV motif (which has anti-inflammatory properties) will improve the efficacy of the hydrogel the method of the second aspect as inflammation may occur in the treatment site. Hence, the or each peptide may preferably have the following structure: A.S.L.-$AA_1$-$AA_2$-KPV, where A.S.L. denotes the Aromatic Stacking Ligand, where $AA_n$ denotes amino acid residues in the peptide, and where KPV denotes the KPV motif. It will be appreciated that the above structure is a pentapeptide.

The inventors were surprised to observe that if a peptide in the hydrogel includes an aromatic amino acid, such as phenylalanine, then this resulted in the formation of effective hydrogels under biologically acceptable conditions. This is illustrated by the efficacy of the Phe-Phe dipeptide investigated. Hence, preferably, at least one peptide of the composition used in the method according to the invention comprises at least one aromatic amino acid. By the term "aromatic amino acid", we mean an amino acid comprising a benzene (or other aromatic group) ring in its side chain.

Preferably, more than one of the peptides of the hydrogel comprises at least one aromatic amino acid. Preferably, the or each peptide comprises a plurality of aromatic amino acids. In preferred embodiments, each amino acid of each peptide in the composition is an aromatic amino acid. Therefore, by way of example, in embodiments where the hydrogel comprises a dipeptide, the dipeptide preferably comprises two aromatic amino acids, and where the hydrogel comprises a tripeptide, the tripeptide preferably comprises three aromatic amino acids.

Examples of suitable aromatic amino acids, which could be included in each peptide in the hydrogel include tyrosine, tryptophan, or phenylalanine. However, it is most preferred that the aromatic amino acid in the peptide comprises phenylalanine. While the inventors do not wish to be bound by any hypothesis, they believe that aromatic amino acids comprising an aromatic side chain contribute to side branching between the peptides in the hydrogel. The inventors believe that such side branching considerably enhances the generation of the hydrogel under biologically acceptable conditions, and this produces an improved scaffold for supporting cell tissues.

Accordingly, it is preferred that the hydrogel used in the method of the second aspect comprises a plurality of peptides, or derivatives, or analogues thereof, wherein each peptide comprises at least two amino acid residues, and an aromatic stacking ligand, wherein at least one amino acid comprises an aromatic side chain, and wherein under biologically acceptable conditions, interactions between the stacking ligands cause the hydrogel to form a hydrogel. It is preferred that the amino acid comprising an aromatic side chain is phenylalanine.

Surprisingly also it has been found that peptides containing amino acids with acidic and basic side chains (for example those containing the sequences RGD or RGE) form gels that are less shear sensitive and of higher mechanical strength than those not incorporating such side chains.

Derivatives or analogues of the peptide hydrogel used in the method according to the invention may include derivatives or analogues that increase or decrease the peptide's half-life in vivo. Examples of derivatives or analogues capable of increasing the half-life of the peptide according to the invention include peptoid derivatives, D-amino acid derivatives of the peptides, and peptide-peptoid hybrids.

The peptide used in the invention may be subject to degradation by a number of means (such as protease activity in biological systems). Such degradation may limit the bioavailability of the peptide, and hence the ability of the peptide to achieve its biological function. There are wide ranges of well-established techniques by which peptide derivatives or analogues that have enhanced stability in biological contexts can be designed and produced. Such peptide derivatives may have improved bioavailability as a result of increased resistance to protease-mediated degradation.

Preferably, a peptide derivative or analogue suitable for use according to the invention is more protease-resistant than the peptide from which it is derived. Protease-resistance of a peptide derivative and the peptide from which it is derived may be evaluated by means of well-known protein degradation assays. The relative values of protease resistance for the peptide and the peptide derivative or analogue may then be compared.

Peptoid derivatives of the peptide hydrogel used in the invention may be readily designed from knowledge of the structure of the peptide. Peptoid compounds have two properties that make them suitable for use as peptide derivatives/analogues according to the invention:

(i) In peptoid residues, no hydrogen bond involving the NH would be possible.
(ii) The peptoids are resistant to enzymatic degradation.

Commercially available software may be used to develop peptoid derivatives according to well-established protocols.

Retropeptoids, (in which all amino acids are replaced by peptoid residues in reversed order) are also able to mimic peptides. A retropeptoid is expected to bind in the opposite direction in the ligand-binding groove, as compared to a peptide or peptoid-peptide hybrid containing one peptoid residue. As a result, the side chains of the peptoid residues are able to point in the same direction as the side chains in the original peptide.

As discussed herein, the inventors have surprisingly found that the hydrogel used in the method according to the invention forms a stable hydrogel due to the presence of the aromatic stacking ligand.

By the term "aromatic stacking ligand", we mean an aromatic molecule comprising at least one benzene ring, or a related planar, cyclic structure with a delocalised π electron structure, such as pyridine, furan or thiophene or, more generally, ligands that can be covalently attached either to the N or C terminus or side chain of amino acids in a peptide sequence and, which preferably adhere to the 4n+2 (Huckel) rule. It is preferred that the stacking ligand is adapted to interact with at least one other aromatic stacking ligand. Hence, the molecules are able to self-assemble with each other. Surprisingly, such self-assembly of the stacking ligands results in the self-assembly of the peptides to which they are attached. As the peptides assemble together, the hydrogel is formed under biologically acceptable conditions.

Examples of a suitable aromatic stacking ligand, which may be attached to the peptide in the hydrogel used in the method of the invention include any aromatic compound, which comprises at least one benzene ring. The skilled technician will appreciate that there are many different types of aromatic compounds available that could be attached to the peptide in the hydrogel, and which would interact with each other to form a hydrogel. However, examples of suitable aromatic stacking ligand to which the peptide may be attached include benzoyl (Bz) or carboxybenzoyl (Cbz), both of which are common protecting groups used in peptide synthesis, and which will be known to the skilled technician.

However, a preferred aromatic stacking ligand comprises Fmoc (fluorenylmethoxycarbonyl), which is another type of protecting group used in peptide synthesis, the structure of which is shown in FIG. 4. As shown in FIG. 1a, which is a Circular Dichroism (CD) spectrum, so-called π-stacking (or π-π interactions) between the fluorenyl groups on an Fmoc aromatic group gives rise to a peak at approximately 308 nm. While the inventors do not wish to be bound by any hypothesis, they believe that such π-stacking between the Fmoc groups enables and encourages hydrogen bonding to occur between the peptides in the hydrogel used in the method according to the invention. The inventors believe that such hydrogen bonding between the peptides causes the formation of structures, which resemble β-sheets between the plurality of peptides in the hydrogel. The inventors believe that these β-sheet-type structures cause the formation of the hydrogel. Another advantage of Fmoc is that it is thought to have anti-inflammatory properties, which will have significant advantages as the hydrogel is used in medical applications.

Hence, it is preferred that the method comprises administering to the treatment site, a hydrogel which comprises comprise a plurality of peptides, or derivatives, or analogues thereof, wherein each peptide comprises at least two amino acid residues attached to Fmoc.

Preferably, under biologically acceptable conditions, interactions between the Fmoc structures cause the formation of the hydrogel. A preferred peptide is Fmoc-Phe-Phe. Another preferred peptide comprises a mixture of Fmoc-Phe-Phe and Fmoc-Gly-Gly.

Another preferred aromatic stacking ligand, which may be attached to the peptide in the hydrogel used, comprises an aromatic amino acid, i.e. an amino acid residue comprising an aromatic side group (i.e. at least one benzene ring). Accordingly, in this embodiment, because the aromatic stacking ligand is itself an aromatic amino acid, and because it is attached to at least two other amino acid residues, the hydrogel comprises at least three amino acid residues. Where the ligand is an aromatic amino acid attached to a tripeptide, the hydrogel comprises a tetrapeptide, and so on.

Examples of suitable aromatic amino acids may include tyrosine, tryptophan, or phenylalanine, or less common aromatic amino acids such as di-hydroxy-phenylalanine (DOPA), or other natural or non-natural amino acids with aromatic side chains. Hence, the hydrogel used in the method according to the invention may comprise a plurality of peptides, or derivatives, or analogues thereof, wherein each peptide comprises at least two amino acid residues attached to an aromatic amino acid residue.

In addition to the peptides, which comprise at least two amino acid residues, in the hydrogel used in the method, the inventors also investigated modifying the hydrogel used in the method according to the invention by adding further components thereto. They added various additives to the hydrogel components, and found that it was possible to further tailor the structural and functional characteristics of the resultant hydrogel formed under biologically acceptable conditions, such characteristics depending on the intended use of the hydrogel. Therefore, the hydrogel may further comprise a bioadditive.

By the term "bioadditive", we mean a compound exhibiting biologically active functionality.

By way of example, the bioadditive may be adapted to promote or improve cell adhesion. It is known that cells respond favourably to positive charges. Hence, it is preferred that the bioadditive is positively charged. The bioadditive may comprise at least one further amino acid, or a peptide. Therefore, the bioadditive may comprise a positively charge amino acid residue, for example, arginine, histidine, or lysine. The inventors have demonstrated in the Examples that the addition of lysine (K) significantly improves cell adhesion.

It is preferred that the bioadditive itself comprises an aromatic stacking ligand, which may be provided so that the bioadditive is able to form hydrogen bonds with the peptides of the hydrogel used according to the invention. Suitable aromatic stacking ligands, are as described hereinbefore. Hence, a preferred aromatic stacking ligand comprises Fmoc. As mentioned herein, Fmoc is thought to have anti-inflammatory properties. In another embodiment, the bioadditive may be Fmoc.

Hence, the bioadditive may preferably have the following structure: A.S.L.-K, where A.S.L. denotes the Aromatic Stacking Ligand, and where K denotes the Lysine residue. It will be appreciated that the above structure is a single amino acid attached to the aromatic stacking ligand. Preferably, the aromatic stacking ligands comprise Fmoc.

Hence, a preferred peptide used in the method in accordance with the invention comprises a mixture of Fmoc-Phe-Phe with Fmoc-Lys.

With all of the above considerations in mind, particularly suitable di- or higher-peptides (incorporating an aromatic stacking ligand) for producing hydrogels in accordance with the invention are as follows:

(i) Fmoc-Phe-Phe either alone or in combination with one or more of Fmoc-Lys, Fmoc-Gly, Fmoc-Gly-Gly, Fmoc-(SEQ. ID. NO. 1), Fmoc-(SEQ. ID. No. 2) or Fmoc-Trp;

(ii) Fmoc-Phe-Phe-Phe;

(iii) Fmoc-Leu-Leu-Leu;

(iv) Cbz-Phe-Phe;

(v) Cbz-Phe-Phe-Phe; and (vi) Cbz-Leu-Leu-Leu.

Generally the amount of each di- or higher- peptide (incorporating the aromatic stacking ligand) and (if present) amino acid incorporating an aromatic stacking ligand will each be in the range of 1 to 50 mM/L, more preferably 5-30 mM/L.

The hydrogels may be formed by increasing the pH of a solution of the gel-forming components to 9-11 (more preferably about 10) and then reducing the pH into the range 6-8 (such that gel formation occurs. More preferably gel formation occurs about pH 7. Gel formation may be effected at ambient temperature or on incubation, e.g. at a temperature of up to 40° C. (for example 35°-40° C.).

It will be appreciated that the hydrogel used in the method of the second aspect may be either used effectively in a number of different physical forms. For example, in one embodiment, the method may comprise administering to the treatment site a liquid hydrogel precursor composition in the form of a solution, which may then be induced to form the hydrogel. Alternatively, in another embodiment, the method may comprise administering to the treatment site the already formed hydrogel composition. The inventors believe that each of these embodiments is an important aspect of the invention, which may be used with the method of the second aspect.

Hence, in a third aspect, there is provided a liquid hydrogel precursor composition comprising a plurality of peptides, or derivatives, or analogues thereof, wherein each peptide comprises at least two amino acid residues and an aromatic stacking ligand, and a physiologically acceptable excipient.

Preferably, the hydrogel precursor composition may be induced to form a hydrogel, for example, by reducing the temperature to below the critical gelation temperature.

Figure 2:
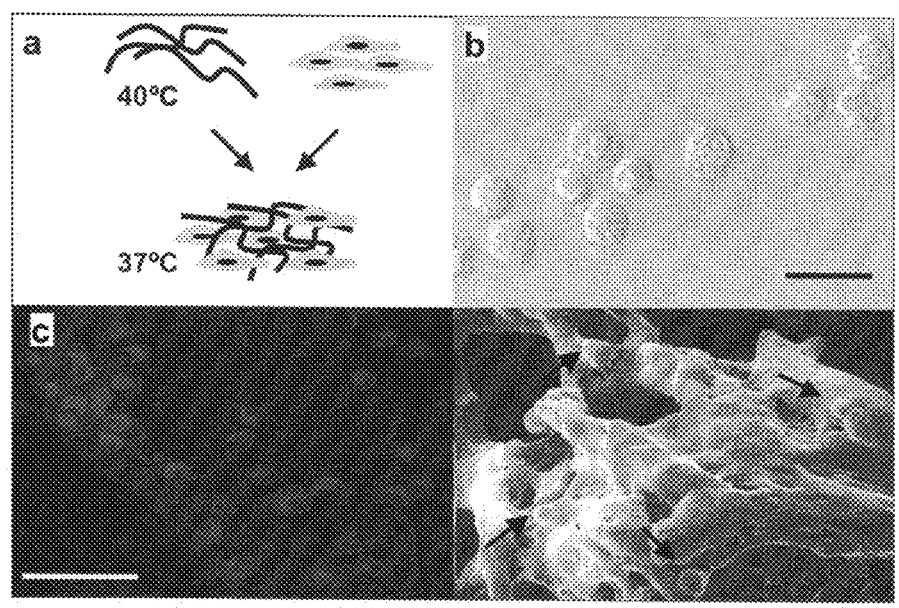
FIG. 2 shows chondrocyte cell culture in self-assembled Fmoc-dipeptide hydrogel scaffolds in accordance with various embodiments of the present invention. (a): scheme representing formation of gel in the presence of cells (b): cell morphological phenotype is retained on surface of gel Fmoc-Phe-Phe-OH (c): two photon fluorescence microscopy reveals the presence of DAPI stained cells throughout the gel Fmoc-Phe-Phe-OH (d): ESEM shows the structure of gel Fmoc-Phe-Phe-OH+Fmoc-Gly-Gly-OH with chondrocytes attached (arrows).

As mentioned herein, prior art hydrogels have only been made at acidic pH, and it will be appreciated that low pHs are unsuitable for medical applications. Therefore, because the hydrogel according to the invention forms in a physiological excipient under biologically acceptable conditions, the inventors wanted to assess whether functional cues or moieties could be incorporated into the hydrogel's structure so that they could be adapted for medical uses. The inventors therefore tested the hydrogel formed from Fmoc-Phe-Phe (and mixtures therewith) for its stability in cell culture conditions, and its ability to support cell cultures or tissues. As discussed in the Examples, microscopic images shown in FIG. 2 confirmed that the hydrogels tested had the surprising ability to organise cells into a three-dimensional architecture. The inventors have therefore observed that the hydrogels according to the invention are surprisingly suitable for culturing and supporting cells therein. The inventors then conducted statistical analysis of data used in an MTT Assay, which further confirmed the surprising finding the cell growth actually continued for the entire time measured, i.e. up to 7 days.

Therefore, it is preferred that the hydrogel of the first aspect or that used in the method according to the second aspect, or the precursor composition of the third aspect is adapted to support at least one cell, to thereby form a physiologically stable cell-supporting medium or cell scaffold. Hence, the hydrogel used in the method of the first aspect, or the composition of the second or third aspect may be seeded with at least one cell.

Hence, according to a fourth aspect of the present invention, there is provided a cell-supporting medium comprising the hydrogel of the first aspect, or that used in the method according to the second aspect or the precursor composition of the third aspect, and at least one cell.

The cell-supporting medium of the fourth aspect may be referred to as a cell-hydrogel scaffold. Preferably, the cell-supporting medium is adapted to support a plurality of cells. Preferably, the or each cell is biochemically functional in vivo. Accordingly, the plurality of cells may form a cell culture or a tissue.

As the hydrogel precursor composition in the third aspect is a liquid, at least one cell may be suspended therein. As the hydrogel composition in the first aspect is a gel, at least one cell may be supported on and/or in the structure of the hydrogel, which therefore acts as a supporting scaffold structure.

The inventors investigated various methods for preparing the cell-supporting medium according to the fourth aspect.

Hence, in a fifth aspect, there is provided a method of preparing a cell supporting medium according to the fourth aspect, the method comprising the steps of:

(i) contacting either a hydrogel of the first aspect, or that used in the method of the second aspect, or the precursor composition of the third aspect with at least one cell; and (ii) exposing the hydrogel or composition to conditions such that the at least one cell is supported on and/or in a hydrogel, thereby forming a cell-supporting medium.

It will be appreciated that the method according to the fifth aspect may be carried out in situ in the treatment site, or remote from the treatment site, and then transferred thereto.

The skilled technician will appreciate how to culture various cell types with the hydrogel or precursor. Hence, it will be appreciated that the specific details of the methodologies (culture time, temperatures, growth media etc) used will depend on the type of cell involved, and the final use of the cell-supporting medium (ie. the scaffold). By way of the example, the Example provides details of how to culture chondrocytes and to produce a chondrocyte cell scaffold.

In one embodiment, step (i) of the method according to the fifth aspect may comprise contacting the liquid hydrogel precursor composition according to the third aspect with the at least one cell. In another embodiment, step (i) of the method according to the fifth aspect may comprise contacting the hydrogel composition according to the first aspect with the at least one cell. The nature of step (ii) of the method will be determined by whether the composition in step (i) is in liquid form or a hydrogel.

Hence, in one embodiment, the method may comprise exposing the composition of the first aspect to conditions such that a hydrogel is formed in step (i) prior to contacting the at least one cell therewith. Such conditions may comprise lowering the temperature of the composition to below the critical gelation temperature, e.g. less than 40° C. The inventors investigated this embodiment of the method, and surprisingly found that cells in a culture media were rapidly taken up by the hydrogel in step (ii) of the method to form the cell-supporting medium. They found that the cell culture distributed itself on and throughout the hydrogel in step (ii). The inventors envisage that this embodiment will have great utility in the method of the second aspect.

In an alternative embodiment, the composition may be initially maintained under conditions in which it is in the form of the liquid precursor in step (i) of the method, to which the at least one cell is added in step (ii). Hence, the method may comprise initially exposing the composition in step (i) to conditions in which it is substantially liquid (i.e. not a hydrogel). For example, the composition may be exposed to a pH or temperature or ionic strength at which the compound is liquid. For example, the composition may be exposed to a temperature above the critical gelation temperature of about 40° C. or more, such that it liquifies. The method may then comprise the step of contacting the at least one cell with the liquid precursor in step (i). After step (i), step (ii) preferably comprises exposing the liquid precursor composition to conditions in which it forms a hydrogel. For example, the temperature may be cooled to about 37° C., or the pH may be adjusted such that the hydrogel is preferably formed with cells distributed throughout. The hydrogel which forms, in which the at least one cell is supported is referred to as the cell-supporting medium or cell scaffold. Again, the inventors believe that this embodiment will have great utility in the method of the second aspect.

The composition according to the first or third aspect, or the medium according to the fourth aspect may be used in a number of ways. A common problem with many wounds or tissue degenerative disorders is that a cavity or space may be formed in the body of the individual being treated, and this cavity or space will need to be repaired using the composition of cell support medium. Hence, the composition or medium may be prepared either in vitro or in vivo. Furthermore, the composition or medium may be prepared either: (i) in situ (in the wound itself); or (ii) remote from the wound, and then transferred to the area to be treated after it has been prepared.

Preferably, the method according to the fifth aspect is used to prepare the cell-supporting medium. Therefore, in one embodiment, the hydrogel or composition according to the third aspect is preferably administered to the area to be treated (wound, cavity, or degenerated area). It will be appreciated that the composition according to the third aspect is in liquid form and the composition according to the first aspect is in the form of a hydrogel. Once the composition is in position in the area to be treated, at least one cell is then contacted therewith as in step (i) of the method according to the fifth aspect. If the composition is a hydrogel, then at least one cell can be contacted therewith to allow the cell scaffold to form. If the compound is in the form of the liquid hydrogel precursor, then as it cools to body temperature, it will form the hydrogel.

In another embodiment, the cell-supporting medium may be prepared remote from the wound (eg. in the lab), and is then preferably administered to the area to be treated. In this approach, the gel would be formed in a pre-determined three-dimensional shape for example, by using a mould, and cells may either be added prior to the gelation process or after the gel has formed. The pre-formed gel may then be implanted in the body where the patient's cells migrate into the gel scaffold. Examples of this use would be in tissues, which have a migratory capacity and/or those, which are responsible for tissue remodelling. Examples are skin, bone, and peripheral nerves. The implant may also be supplemented with further cells externally by the medical practitioner. In addition, other factors, which may simulate cell and preferably tissue growth, may be added to the implant, for example, growth factors.

Preferably, the cell supporting medium according to the fourth aspect, whether prepared in situ in the area to be treated, or remote from it, is suitably maintained to allow the at least one cell to divide to form a culture or tissue therein. Accordingly, it will be appreciated that the hydrogel acts as a supporting scaffold for the tissue and thereby allows repair of the wound, or regeneration of the damaged tissue.

The inventors believe that the method according to the first aspect, may be used in wide variety of different, medical treatment methods, such as tissue regeneration/engineering applications, controlled stem cell differentiation, and in wound healing. The types of tissues and wound which could be treated are varied, and hence, it will be appreciated that the invention is not limited to any specific type of cell, which could be supported and cultured on the hydrogel administered to the treatment site. However, by way of example, suitable cells, which may be supported in the hydrogel include epithelial cells (e.g., hepatocytes), neurons, endothelial cells, osteoblasts (bone cells), chondrocytes (cartilage cells), fibroblasts, smooth muscle cells, osteoclasts, keratinocytes, nerve progenitor cells, Schwann cells, stem cells, macrophages, islet cells, and tumour cells, etc.

The cell type contacted with the composition or cell-supporting medium will depend on the type of wound being repaired, or the type of tissue being regenerated. Therefore, by way of example, if the wound is in skin, then at least one skin cell may be contacted with the hydrogel, composition or cell-supporting medium. If the wound is in bone, then at least one bone cell or osteoblast is preferably contacted with the hydrogel, composition or cell-supporting medium. If the wound is in cartilage, then at least one chondrocyte is preferably contacted with the hydrogel, composition or cell-supporting medium. If the eye tissue has been damaged, it may be required to contact the hydrogel, composition or cell-supporting medium with eye stem cells. It will be appreciated that different types of cell type may be contacted with the hydrogel, composition, or cell supporting medium, if necessary.

As discussed in the Examples, the inventors focussed their research on investigating the efficacy of the hydrogel cell-supporting medium (or scaffold) according to the fourth aspect to support cartilage cells. Hence, it is preferred that the at least one cell is a chondrocyte. This would be advantageous, if the treatment site is a site in which cartilage has been damaged or lost. However, the at least one cell may be an osteoblast or bone cell. This would be useful if the site being treated is bone. The osteoblast may be autologous or autogenous.

Alternatively, the at least one cell may be a stem cell, which may be either mesenchymal, or haematopoeic, or embryonic, or cloned. The inventors believe that the ability to culture and support a wide variety of cells such as chondrocytes, osteoblasts and stem cells, will be of significant importance in many aspects of medicine.

The method according to the second aspect may comprise use of the composition according to either the first or third aspect, or of the cell-supporting medium according to the fourth aspect. The composition or cell supporting medium may be combined in formulations having a number of different forms depending, in particular on the manner in which the formulation is to be used. It will be appreciated that the vehicle of the composition of the invention should be one which is well-tolerated by the subject to whom it is given, and preferably enables efficient delivery of the composition to a target site. Thus, for example, the composition may be in the form of a liquid (composition according to the third aspect), or gel or hydrogel (composition according to the first aspect), or any other suitable form that may be administered to a person or animal.

The inventors believe that the Fmoc peptides described herein may be formulated with a physiologically acceptable excipient to form a medicament. The inventors believe that the prior art does not hint at or even suggest that hydrogels according to the invention may be used as a medicament.

Therefore, according to a sixth aspect of the invention, there is provided a composition according to the first or third aspect, or a cell-supporting medium according to the fourth aspect, for use as a medicament.

In particular, the inventors envisage the composition of the first or third aspect or cell-supporting medium according to the fourth aspect will have major uses in a wide variety of tissue engineering and regeneration applications, and also in wound healing. Such disorders are commonly linked in that they a characterised by tissue damage or loss.

Therefore, according to a seventh aspect, there is provided use of a composition according to the first or third aspect, or a cell supporting medium according to the fourth aspect, for the preparation of a medicament for the treatment of a medical condition characterised by tissue loss/damage.

It will be appreciated that the medicament may be used to treat individuals suffering from a wide variety of disease conditions characterised by tissue loss or damage. Examples include wounds and/or tissue degenerative disorders.

The wound may be chronic or acute. Tissue degenerative disorders that may be treated include neurodegenerative, intervertebral disc disorders, cartilage or bone degeneration such as osteoarthritis, osteoporosis, liver degenerative disorders, kidney degenerative disorders, muscle atrophy.

It will be appreciated that in chronic wounds, it has been described that modulating the pH of the wound may help improve wound healing. The pH in chronic wounds varies between 6 and 8, and the inventors believe that wound healing appears to work best at reduced pH values. Hence, the composition may comprise acidic or basic amino acids (His, Arg. Lys, Glu, Asp), which may help maintain the pH of the hydrogel in the treatment site.

Furthermore, in chronic wounds, the temperature may be a few degrees lower than normal body temperature, i.e. about 32° C. to 34° C. Furthermore, for treating surface organs such as the eye, skin, and so on, etc the preferred temperature will be lower than normal body temperature. However, the composition will need to gel at this temperature range to form the scaffold.

It will be appreciated that the hydrogel of the first aspect, that used in the second aspect, the composition according to the third aspect, or the cell-supporting medium according to the fourth aspect may be used to formulate the medicament of the sixth or seventh aspect. Furthermore, the medicament may be used in the method of treatment according to the second aspect.

The hydrogel, compositions, cell-supporting medium, or medicament according to the invention may be used in a monotherapy (i.e. use of the hydrogel, composition, cell supporting medium, or medicament, alone). Alternatively, the hydrogel, compositions, cell-supporting medium, or medicament according to the invention may be used as an adjunct, or in combination with other known therapies.

In some circumstances, the composition, compound or scaffold according to the invention may be administered by injection into the wound areas. Injections may be intravenous (bolus or infusion) or subcutaneous (bolus or infusion).

The hydrogel, compositions, cell-supporting medium, or medicament may also be incorporated within a slow or delayed release device. Such devices may, for example, be positioned on or adjacent the area to be treated, for example by implantation, and the hydrogel, compositions, cell-supporting medium, or medicament may be released over weeks or even months. Such devices may be particularly advantageous when long-term treatment with the medicament is required and which would normally require frequent administration (e.g. at least daily injection or implant).

It will be appreciated that the amount of hydrogel, compositions, cell-supporting medium, or medicament according to the invention required will be determined by its biological activity and bioavailability, which in turn depends on the mode of administration, the physicochemical properties of the medicament employed, and whether the hydrogel, compositions, cell-supporting medium, or medicament is being used as a monotherapy or in a combined therapy. The frequency of administration will also be influenced by the above-mentioned factors and particularly the half-life of the medicament within the subject being treated.

Optimal dosages to be administered may be determined by those skilled in the art, and will vary with the particular medicament in use, the strength of the preparation, the mode of administration, and the advancement of the disease condition. Additional factors depending on the particular subject being treated will result in a need to adjust dosages, including subject age, weight, gender, diet, and time of administration.

Known procedures, such as those conventionally employed by the pharmaceutical industry (e.g. in vivo experimentation, clinical trials, etc.), may be used to establish specific formulations of the medicament according to the invention, and precise therapeutic regimes (such as daily doses and the frequency of administration).

Generally, a daily dose of between 0.01 μg/kg of body weight and 1.0 g/kg of body weight of the hydrogel according to the invention may be used for the prevention and/or treatment of the specific medical condition. More preferably, the daily dose is between 0.01 mg/kg of body weight and 100 mg/kg of body weight. Daily doses may be given as a single administration (e.g. a single daily tablet). Alternatively, the medicament may require administration twice or more times during a day. As an example, the medicament according to the invention may be administered as two (or more depending upon the severity of the condition) daily doses of between 25 mg and 5000 mg. A patient receiving treatment may take a first dose upon waking and then a second dose in the evening (if on a two dose regime) or at 3 or 4 hourly intervals thereafter. Alternatively, a slow release device may be used to provide optimal doses to a patient without the need to administer repeated doses.

The invention further provides a pharmaceutical composition comprising a therapeutically effective amount of a hydrogel, compositions, cell-supporting medium, or medicament according to the invention. In one embodiment, the amount of the hydrogel is an amount from about 0.01 mg to about 800 mg. In another embodiment, the amount of the hydrogel is an amount from about 0.01 mg to about 500 mg. In another embodiment, the amount of the hydrogel is an amount from about 0.01 mg to about 250 mg. In another embodiment, the amount of the hydrogel is an amount from about 0.1 mg to about 60 mg. In another embodiment, the amount of the hydrogel is an amount from about 0.1 mg to about 20 mg.

The invention also provides a process for making a pharmaceutical composition, the process comprising combining a therapeutically effective amount of a hydrogel, compositions, or cell-supporting medium according to the present invention, and a pharmaceutically acceptable vehicle. A "therapeutically effective amount" is any amount which, when administered to a subject provides prevention and/or treatment of a specific medical condition. A "subject" may be a vertebrate, mammal, domestic animal or human being.

A "pharmaceutically acceptable vehicle" as referred to herein is any physiological vehicle known to those of ordinary skill in the art useful in formulating pharmaceutical compositions. The pharmaceutically acceptable vehicle may be a liquid, and the pharmaceutical composition is in the form of a solution. In a further preferred embodiment, the pharmaceutical vehicle is a gel or hydrogel, and the composition is in the form of a cream or the like. In both cases, the composition may be applied to the treatment site.

The composition may comprise one or more substances, which may also act as lubricants, solubilisers, suspending agents, fillers, glidants, compression aids, or binders. It can also be an encapsulating material. Liquid vehicles are used in preparing solutions, suspensions, emulsions, syrups, elixirs and pressurized compositions. The hydrogel, compositions, cell-supporting medium, or medicament may be dissolved or suspended in a pharmaceutically acceptable liquid vehicle such as water, an organic solvent, a mixture of both or pharmaceutically acceptable oils or fats. The liquid vehicle may contain other suitable pharmaceutical additives such as solubilisers, emulsifiers, buffers, preservatives, sweeteners, flavouring agents, suspending agents, thickening agents, colours, viscosity regulators, stabilizers or osmo-regulators. Suitable examples of liquid vehicles for oral and parenteral administration and implants include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the vehicle can also be an oily ester such as ethyl oleate and isopropyl myristate. Sterile liquid vehicles are useful in sterile liquid form compositions for parenteral administration. The liquid vehicle for pressurized compositions can be halogenated hydrocarbon or other pharmaceutically acceptable propellent.

In cases where it is desired to inject or implant the hydrogel, compositions, cell-supporting medium, or medicament directly to the treatment site, liquid pharmaceutical compositions which are sterile solutions or suspensions can be utilized by for example, intramuscular, intrathecal, epidural, intraperitoneal, intravenous and particularly subcutaneous, intracerebral or intracerebroventricular injection. The hydrogel may be prepared as a sterile hydrogel composition that may be dissolved or suspended at the time of administration using sterile water, saline, or other appropriate sterile injectable medium. Vehicles are intended to include necessary and inert binders, suspending agents, lubricants, sweeteners, preservatives, dyes, and coatings.

It is preferred that the hydrogel, compositions, cell-supporting medium, or medicament according to the invention may be implanted in the form of a sterile solution or suspension or gel or hydrogel containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like. Preferably, the hydrogel is implanted either in liquid or solid (hydrogel) composition form. Compositions suitable for implants include liquid forms, such as solutions, syrups, elixirs, and suspensions.

It will be appreciated that the self-assembling hydrogels according to the invention have a wide range of medical applications, for use in the method of the second aspect. In addition, the inventors also explored the use of the self-assembling hydrogel in a range of non-medical applications, for example, in 3D cell culturing, in vitro toxicity testing, understanding cell/extracellular matrix interactions, studies of mechanical loading effects on cells, and cell study or metastasis models.

Therefore, the inventors made a comparison of current materials, which are available for in vitro 3D cell studies, with the hydrogel used in the method according to the first aspect of the invention. The currently available materials that the inventors tested included: PURAMATRIX; Bovine Collagen; Agarose; and chitosan.

Hence, according to a further aspect, there is provided use of a composition according to the cell-supporting medium according to the fourth aspect for studying a cell culture in vitro.

The comparison showed that PURAMATRIX can be somewhat difficult to handle, and initially somewhat toxic to cells (pH 3-4). Furthermore, bovine collagen, agarose and chitosan are unsatisfactory model systems due to batch-to-batch variations of the material, difficulty in handling and/or significantly different properties to the in vivo extracellular matrix. It is preferred that the use comprises initially preparing a hydrogel from the self-assembling peptides, and then adding a cell culture thereto, so that the cell behaviour under conditions that mimick in vivo growth environment can be studied. Hence, preferably the cell culture grown on the cell-supporting medium is substantially 3D. The growth experiments may be carried out in 20 or 96 well plate format and may have applications in 3D cell culture, in vitro toxicity testing, understanding cell/extracellular matrix interactions, controlled stem cell differentiation, studies of mechanical loading effects on cells, and the study of metastasis models. Currently, PURAMATRIX, Bovine Collagen, Agarose or chitosan are used, which the inventors have found to be significantly inferior cell supporting medium according to the fourth aspect.

All of the features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying diagrammatic drawings.

EXAMPLE 1

The inventors conducted a series of experiments to investigate the design and preparation of hydrogel scaffolds, and their use in supporting tissue cell cultures. The inventors believed that such hydrogel scaffolds could have significant uses in biological tissue regeneration and engineering.

Materials and Methods (1) Preparation of Peptide Hydrogels

Fmoc peptides (from BACHEM Ltd) were weighed out into 4 ml glass vials. 2 ml purified water was added followed by sonication for 30-60 seconds. 0.5M NaOH solution was added in 50 µl droplets until a clear solution was formed. 0.1M HCl was added to the solution by stepwise addition of 50 µl followed by mixing using a vortex. pH values were estimated by transferring a spatula tip of hydrogel onto universal indicator paper.

(2) Cell Cultures

Bovine chondrocytes were isolated from cartilage of the proximal side of the metacarpalphalangeal joint, washed in PBS and incubated overnight in Dulbeccos Modified Eagles Medium (DMEM) supplemented with 10% foetal calf serum, 100 units ml$^{-1}$ penicillin/streptomycin and 0.85 mM ascorbic acid. The cartilage was finely chopped and incubated with pronase type E (700 units ml$^{-1}$) (BDH Ltd., Poole, UK) in medium for 2 h followed by collagenase type 1a (300 units ml$^{-1}$) (SIGMA-ALDRICH Co. Ltd., Poole, UK) in medium for 2 h. The cell suspension was centrifuged at 1500 rpm for 5 min to pellet the cells. The cells were washed twice in medium and seeded directly onto the peptide scaffolds (and tissue culture plastic control) or encapsulated within the scaffolds during the gelation stage at a cell density of 5×10$^5$ ml$^{-1}$ in medium. The cultures were maintained in an incubator at 37° C. with a humidified atmosphere of 5% CO$_2$ for up to 4 weeks. Chondrocytes were used up to passage 5.

(3) MTT Assay for Cell Proliferation

Cells were cultured for 1, 3 and 7 days. A 5 mg/ml of MTT reagent in acidified isopropanol was used at a dilution factor of 1:10 in culture medium. This was added to cells and incubated for 4 hours. Culture medium was then removed and the reduced MTT reagent removed by dissolution with acidified isopropanol. Optical density of the reagent was then measured using a LABSYSTEMS ASCENT colourimetric plate reader at 570 nm. By preparing a standard curve of MTT reduction against cell number, optical density values can be converted into actual cell numbers.

(4) Microscopy CryoSEM

Microscopy CryoSEM was performed using a PHILIPS XL30 ESEM-FG equipped with an OXFORD INSTRUMENT ALTO 25000 Cryotransfer system. ESEM was performed using a PHILIPS/FEI XL30 FEG-ESEM equipped with a Peltier effect cooling stage. The Confocal/multiphoton is a BIORAD 1024MRC connected to an inverted NIKON TE300 microscope. The laser for FITC is an AMERICAN LASER Corp Krypton Argon multiline 25 mW laser with 488 nm, 568 nm and 648 nm laser lines. The emission filter used was a 522df35, the DAPI laser was a Ti-Sapphire Spectra-Physics Tsunami multiphoton laser at 740 nm. The emission filter is 450/40, the lens was a NIKON 40X 1.3NA oil Plan Fluor objective.

(5) Preparation of Fmoc-Dipeptides

The inventors prepared using standard techniques an Fmoc capped dipeptide, Fmoc-Phe-Phe and prepared hydrogels in accordance with Table 1. Referring to FIG. 1e, there is shown the standard formula of the dipeptide, which shows the position of R1 and R2, as used in Table 1.

TABLE 1

Properties of a self-assembled Fmoc-dipeptides

| Entry | Fmoc-Peptide | R1 | R2 | pH | Concentration (mM) |
|---|---|---|---|---|---|
| 1 | Phe—Phe | CH$_2$—C$_5$H$_6$ | CH$_2$—C$_5$H$_6$ | 4-8 | 2.9-30.0 |
| 2 | Gly—Gly + Phe—Phe | | | 4-8 | 2.2-30.0 |
| 3 | Phe—Phe + Lys | | | 4-8 | 3.7-30.0 |

(6) Preparation of Hydrogel Scaffolds

Self-assembled scaffolds were prepared by first suspending the Fmoc-dipeptide in purified water. Upon increase of the pH by addition of concentrated NaOH (thus de-protonating the carboxylic acid group) to a value of >8, a clear solution was obtained. To this solution, concentrated hydrochloric acid was added drop wise until the pH of the solution became 7, at which point a clear, self-supporting gel was formed.

The circular dichroism spectrum of Fmoc-Phe-Phe-OH was collected on a Jasco J-810 spectrometer, using a 0.5 mm cuvette, 190-350 nm, with a 1 nm slit width and 4 second accumulation and 3 acquisitions. The gel was formed at 10 mM/L as previously described.

The results are shown in FIG. 1.

The minima at 218 nm indicates the formation of a β-sheet structure and the minima at 305 nm is due to the Fmoc group (1A). Fluorescence spectrum of Fmoc-Phe-OH as a solution indicates that the monomer fluoresces at 320 nm after excitation at 290 nm, when this is a precipitate the emission peak shifts to 330 nm. The gel formed by Fmoc-Phe-Phe-OH has also has an emission peak at 330 nm, this shift is an indicator of excimer formation where Fmoc groups are close enough to form dimers. The additional broad peak observed in the Fmoc-Phe-Phe-OH gel spectrum indicates that higher order aggregates have been formed (1B). A putative model of the structure formed is presented in 1C and D, in this model Fmoc groups stack over one another creating π-π interactions, while the β-sheets form anti-parallel to one another with hydrogen bonding (1D). This can form a tubular structure due to the inherent twist present in βsheets and the arrangement of several β-sheets next to one another (1C).

(7) Stability of Hydrogel Scaffolds In Vivo

For these hydrogels to have applications in biomedicine, it is essential that they are able to withstand near neutral pH values and also high ion concentrations. Fmoc-Phe-Phe, which is a very hydrophobic peptide formed a stable gel at pH 7 as summarised in Table 1. It was then assessed whether the gel properties could be tuned using mixtures of different peptides. As a starting point, Phe-Phe was mixed with the dipeptide Gly-Gly in different ratios. This is shown as entry 2 in Table 1. It was found that stable gels were obtained at pH 7 down to 25 mol % of 7. Interestingly, the 50:50 mixture of Phe-Phe with Gly-Gly formed a more stable gel compared to that of pure peptide material (Phe-Phe). Furthermore, this mixture liquefied into a clear solution by slightly increasing the temperature to 40° C. Upon cooling to 37° C., the hydrogel was reformed, which is a useful transition temperature for applications involving cells (as shown in FIG. 2a).

It was then assessed whether functional cues or moieties could be incorporated into the hydrogel scaffold structures. It is known that cells respond favourably to positive charges. Hence, the inventors tested the addition of a positively charged Fmoc amino acid (i.e. lysine). This is shown as entry 3 in Table 1. The inventors hypothesised that the lysine residues would be incorporated into the Fmoc π-stack thus giving rise to a distribution of charged groups throughout the structure. As summarised in Table 1, the mixture of Phe-Phe composition with Fmoc-Lys was subsequently tested for its stability in cell culture conditions, and it was found to retain its gel like structures when placed in culture media and incubated at 37° C.

(8) Preparation of a 3D Culture of Chondrocytes on the Hydrogel Scaffold

Finally, all three gels prepared (ie. entries 1, 2 and 3) were tested for their ability to support proliferation and retention of phenotype of bovine chondrocytes. For entries 1 and 2, cells in culture media were seeded on top of the preformed gel, and the culture media was rapidly taken up by the hydrogel. For entry 3, cells were incorporated into the gel by mixing with the appropriate Fmoc-peptide solution that was liquefied by slightly increasing the temperature to 40° C. Upon cooling to 37° C., the hydrogel was reformed with cells distributed throughout (as shown by the arrows in FIG. 2d).

During cell culture of up to 7 days, chondrocytes were found to retain morphological phenotype and to proliferate on all three gels tested. FIG. 2b shows chondrocyte cells on the surface of gel entry 1. The rounded cell shape is the typical phenotype for chondrocytes. This observation suggests that this hydrogel scaffold would be suitable for 3D tissue culture of these cells in vitro or for cartilage regeneration in vivo. Two-photon fluorescence microscopy was used to observe samples stained with DAPI, a fluorescent nucleic acid stain that enables visualisation of cell nuclei. This experiment confirmed the presence of cells throughout the gel matrix (as shown in FIG. 2b). ESEM allows for interrogation of the hydrogel structures while hydrated, and revealed a number of rounded features of 10-20 micron in diameter, thought to be chondrocyte cells (as shown in FIG. 2c).

Figure 3:
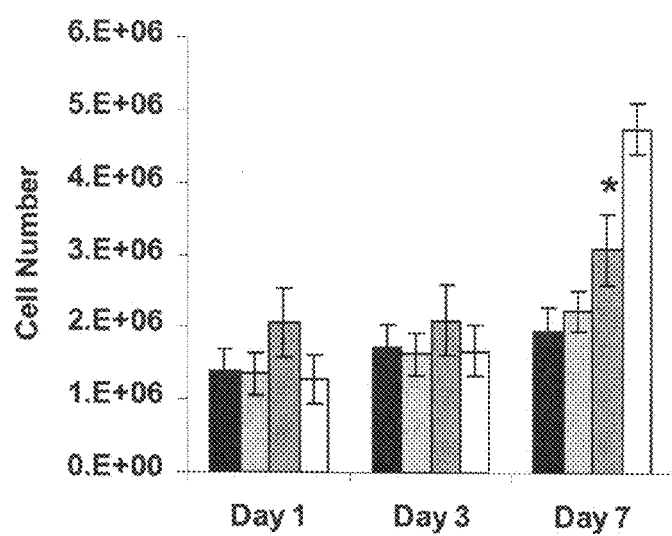
FIG. 3 shows a calorimetric assay (MTT Assay) which shows that the number of surviving cells observed at three different time up to 7 days has a continuous cell growth in accordance with various embodiments of the present invention. Black=hydrogel 1 (Phe-Phe); Light grey=hydrogel 2 (Gly-Gly+Phe-Phe); Dark grey=hydrogel 3 (Phe-Phe plus Lys); White=tissue culture plastic control. Error bars represent standard deviations of mean values where n=3.

The number of metabolically active cells in the scaffold was then determined by using a simple calorimetric assay (MTT). Continuous cell growth was measured at three different time points up to 7 days (as shown in FIG. 3). These experiments revealed that the three gels 1-3 shown in Table 1 support cell proliferation, with gels 1 and 2 showing similar growth profiles. However, gel 2 (i.e. Fmoc-Phe-Phe mixed with Fmoc-Lys) showed significantly more cells after 7 days (p<0.05). While the inventors do not wish to be bound by hypothesis, they believe that this observation may be related to the incorporated cationic Fmoc-Lys residues into the structure of gel 3.

EXAMPLE 2

Starting with the promising results produced in Example 1, i.e. Phe-Phe dipeptides were shown to self-assemble into stable hydrogels, the inventors wanted to investigate further how the design of the self-assembling peptides could be modified to produce other stable hydrogels under physiological conditions.

The inventors thought it would be sensible to retain the two consecutive phenylalanine residues in the peptide, but introduce a third amino acid immediately after the Fmoc cap and before the Phe-Phe. Hence, the inventors produced four tripeptides each of which consisted of Fmoc-X-Phe-Phe, where X=Ala, Val, Leu, Phe. In addition, the inventors also made the tripeptide: Fmoc-Leu-Leu-Leu.

The five tripeptides all formed stable hydrogels as shown in Table 2 below.

TABLE 2

A number of further Fmoc-amino acid/di-peptide combinations that formed hydrogels

| Entry | Fmoc-AA | Di-peptide | Gel formed? |
|---|---|---|---|
| 1 | Ala | Phe—Phe | ✓ |
| 2 | Val | Phe—Phe | ✓ |
| 3 | Leu | Phe—Phe | ✓ |
| 4 | Phe | Phe—Phe | ✓ |
| 5 | Leu | Leu—Leu | ✓ |

[a] mixture of Fmoc-peptides formed
[b] 60 μmol starting materials was used

EXAMPLE 3

Table 3 below identifies various peptide derivatives (incorporating an aromatic stacking ligand) and mixtures thereof that formed gels at a pH of 6-8 at the indicated concentrations:

TABLE 3

| Component 1 | Conc. mM/L | Component 2 | Conc. mM/L | pH | Gel? |
|---|---|---|---|---|---|
| Fmoc-Gly-Gly-OH | 10-40 | — |  | 3-5 | ✓ |
| Fmoc-Gly-Gly-OH | 10-20 | Fmoc-Lys-OH | 10-20 | 5 | ✓ |
| Fmoc-Ala-Ala-OH | 40 | — |  | 3 | ✓ |
| Fmoc-Phe-Phe-OH | 10 | — |  | 7 | ✓ |
| Fmoc-Phe-Phe-OH | 4-16 | Fmoc-Lys-OH | 16-4 | 7 | ✓ |
| Fmoc-Phe-Phe-OH | 10 | Fmoc-Gly-Gly-OH | 10 | 7 | ✓ |
| Fmoc-Phe-Phe-OH | 7.5 | Fmoc-(SEQ. ID. NO. 1)-OH | 7.5 | 7 | ✓ |
| Fmoc-Phe-Phe-OH | 7.5 | Fmoc-(SEQ. ID. NO. 2)-OH | 7.5 | 7 | ✓ |
| Fmoc-Phe-Phe-OH | 10-20 | Fmoc-Gly-Gly-OH | 10-20 | 7 | ✓ |
| Fmoc-Phe-Phe-OH | 10 | Fmoc-Trp-OH | 10 | 7 | ✓ |
| Fmoc-Phe-Phe-Phe-OH | 5-20 | — |  | 7 | ✓ |
| Fmoc-Phe-Gly-OH | 20 | — |  | 3-5 | ✓ |
| Cbz-Phe-Phe-OH | 10-30 | — |  | 6-8 | ✓ |
| Fmoc-Phe_OH | 10-20 | Fmoc-Lys-OH | 10-20 | 3-5 | ✓ |
| Fmoc-Leu-Gly-OH | 20 | — |  | 2 | ✓ |
| Cbz-Leu-Leu-Leu-OH | 5-20 | — |  | 7 | ✓ |

Table abbreviations Fmoc—fluorenylmethyoxycarbonyl, Cbz—carboxybenzyl

EXAMPLE 4

An initial 2D culture of human adult dermal fibroblasts was carried out on the surface of 10 mM/L Fmoc-Phe-Phe-OH self-assembled peptide hydrogels and cell phenotype was investigated under inverted light microscope.

Generally, 0.0107 gram of Fmoc-Phe-Phe-OH was weighed in a glass vial and sterilized for 30 minutes by an ultraviolet light with bottles of distilled water, filtered NaOH (Sodium Hydroxide, 0.5 M/L), filtered HCl (Hydrochloric Acid, 0.5 M/L), and relevant apparatus (spatulas, pipettes, Vortex). 2 mL of the sterile distilled water was then added into the glass vial of Fmoc-Phe-Phe, and the mixture was vortexed for a few seconds to create a suspension. Afterwards, approximate 100 μL of NaOH was gradually pipetted into the suspension (20 μL each pipetting) and the mixture was vortexed after every addition of the alkaline. The whole mixture was shaken continually until a homogeneous transparent solution was obtained. The basic peptide solution (pH around 10) was finally neutralized to pH 7 by dropwise addition of HCl and pH values were monitored by a pH meter with a micro-probe.

Figure 5:
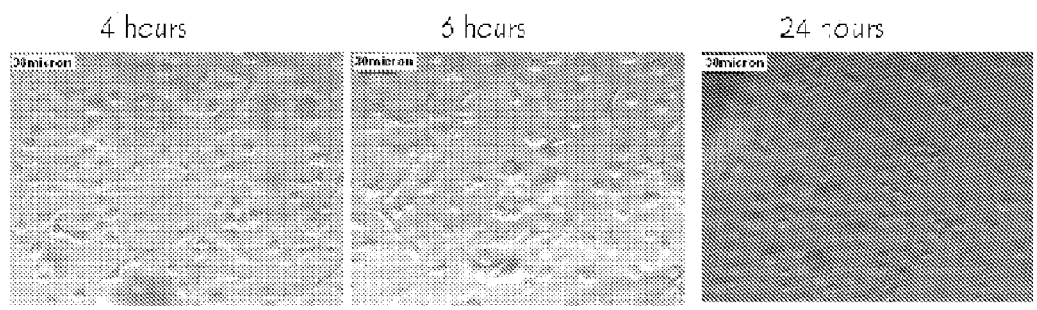
FIG. 5 illustrates the appearances of human adult dermal fibroblasts cultured on top of self-assembled peptide hydrogels of Fmoc-Phe-PheOH at time points of 4 hours (spreaded), 6 hours (spreaded) and 24 hours (rounded) in accordance with various embodiments of the present invention.

The above peptide solutions of physiological pH were aliquoted into a 24 well-plate with 500 μL in each well and the well plate was maintained in a 37° C./5% $CO_2$ incubator overnight. The solution underwent a self-assembling to become hydrogels. Human adult dermal fibroblasts in suspension were then poured on top of the self-assembled hydrogels with 1 mL cell suspension for each well. Cell suspensions of 8×10$^4$/mL were used with a serum-free DMEM (Dulbecco's modified Eagle's medium) supplemented by 1% antibiotics/antimicotics. The cell culture was maintained for up to 72 hours in the 37° C./5% CO$_2$ incubator and cell phenotype was observed at different time points. The results are shown in FIG. 5 which shows the appearances of human adult dermal fibroblasts cultured on top of self-assembled peptide hydrogels of Fmoc-Phe-PheOH at time points of 4 hours (spreaded), 6 hours (spreaded) and 24 hours (rounded). Within the first 8 hours of culturing, cell attachment and spreading was observed as cells were flattened on the surfaces and possessing a spindle-like to polygonal phenotype, regardless of the hydrogel types. These originally spreaded cells, however, became rounded with a diameter of around 10 microns between 24 and 72 hours. The phenomenon indicated of a dynamic solid (gel)-liquid (culture medium) interface which formed a malleable, unstable gel surface to wrap and sink cells into the interacted nano-filaments of the gel structure resulting the cells' rounding up.

With 10 mM/L Fmoc-Phe-Phe-OH self-assembled hydrogels, human adult dermal fibroblast were also seeded 3 dimensionally (3D culture) inside the peptide gels. When trapped in a 3D aqueous hydrogel, oval to round cell shape remained for a long term; cells falsely sensed themselves in a cell-cell contact environment therefore proliferation phase for increasing cell population was shut off. Despite proliferation, whether ECM components (proteins and saccharides) were synthesized and secreted by these cells is another way to justify cells' reaction to the material. However, viability of the cells is of necessity to maintain a steady ECM secretion or to restore proliferation after possible cell spreading at later time points.

EXAMPLE 5

In order to coarsely test cell viability, a Live/Dead assay was chosen in which two reagents of EthD-1 and Calcine AM were involved. EthD-1 is able to enter intact cell membranes of living cells and to selectively react with the cells metabolically to form a bright green fluorescence dye, while Calcine AM can only enter broken nucleus membranes of dead cells to stain the nucleus red. With the help of this staining and fluorescence microscope, living and dead cells could be easily visualized therefore viability inside the culture is measured.

For making Fmoc-Phe-Phe-OH peptide solution, 0.0107 gram of Fmoc-Phe-Phe-OH was weighed in a glass vial and sterilized for 30 minutes by an ultraviolet light with bottles of distilled water, filtered NaOH (Sodium Hydroxide, 0.5 M/L), filtered HCl (Hydrochloric Acid, 0.5 M/L), and relevant apparatus (spatulas, pipettes, Vortex). 2 mL of the sterile distilled water was then added into the glass vial of Fmoc-Phe-Phe-OH, and the mixture was vortexed for a few seconds to create a suspension. Afterwards, approximate 100 μL of NaOH was gradually pipetted into the suspension (20 μL each pipetting) and the mixture was vortexed after every addition of the alkaline. The whole mixture was shaken continually until a homogeneous transparent solution was obtained. The basic peptide solution (pH around 10) was finally neutralized to pH 7 by dropwise addition of HCl and pH values were monitored by a pH meter with a micro-probe. The solution was left in a 4° C. refrigerator overnight until usage.

The solution was warmed at room temperature on the day of cell culture for around 1 hour. Human dermal fibroblasts were trypsinised and centrifuged into a loose pellet of 2 million in a centrifuge tube. About 200 μl of complete culture medium (DMEM with 10% bovine fetal serum and 1% antibiotics/antimicotics) was added to the pellet and pipetted to obtain a condensed cell suspension; after which 1800 μl of the Fmoc-Phe-Phe-OH solution was poured into the tube and the whole thing was vortexed gently to get a homogeneous pale-pink viscous solution with 1 million/ml cell density. The cell-containing solution was then transferred to a 24 well-plate with 500 μl in each well. A further 1 ml of complete culture medium was poured onto each cell-peptide solution drop by drop. The self-assembling mechanism was rapidly triggered by medium components and stable hydrogels was formed in seconds.

Figure 6:
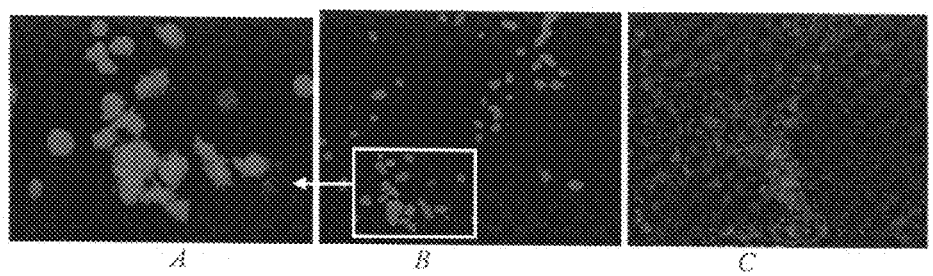
FIG. 6 illustrates the live/dead staining of cells inside Fmoc-Phe-Phe-OH hydrogel in accordance with various embodiments of the present invention. A: magnified from part of figure B, showing partially spreaded cells (3 hours after culture); B: 3 hours after culture; C: 72 hours after culture.

The 3D culture inside Fmoc-Phe-Phe-OH was maintained for 3 days and live/dead staining was done at various time points. The majority of cells were shown to be living in the Fmoc-Phe-Phe-OH hydrogel (stained green) after 72 hours, although cells did not complete spreading in the gels during the first 3 days. A few pictures at 3 hour time-point showed tiny stretched-out filophodia suggesting there might be partial spreading cells. The results are shown in FIG. 6 which shows live/dead staining of cells inside Fmoc-Phe-Phe-OH hydrogel: A: magnified from part of photo B showing partially spreaded cells (3 hours after culture); B: 3 hours after culture; C. 72 hours after culture.

EXAMPLE 6

In order to quantitatively test cell viability in the 3D culture, LDH assay was adopted which tested the amount of lactate dehydrogenase inside cell mitochondria membrane (reflecting cell numbers).

0.0107 gram of Fmoc-Phe-Phe-OH was weighed in a glass vial and sterilized for 30 minutes by an ultraviolet light with bottles of distilled water, filtered NaOH (Sodium Hydroxide, 0.5 M/L), filtered HCl (Hydrochloric Acid, 0.5 M/L), and relevant apparatus (spatulas, pipettes, Vortex). 2 mL of the sterile distilled water was then added into the glass vial of Fmoc-Phe-Phe-OH, and the mixture was vortexed for a few seconds to create a suspension. Afterwards, approximate 100 μL of NaOH was gradually pipetted into the suspension (20 μL each pipetting) and the mixture was vortexed after every addition of the alkaline. The whole mixture was shaken continually until a homogeneous transparent solution was obtained. The basic peptide solution (pH around 10) was finally neutralized to pH 7 by dropwise addition of HCl and pH values were monitored by a pH meter with a micro-probe. The solution was left in a 4° C. refrigerator for overnight until usage.

The solution was warmed at room temperature on the day of cell culture for around 1 hour. Human dermal fibroblasts were trypsinised and centrifuged into a loose pellet of 2 million in a centrifuge tube. About 200 μl of complete culture medium (DMEM with 10% bovine fetal serum and 1% antibiotics/antimicotics) was added to the pellet and pipetted to obtain a condensed cell suspension; after which 1800 μl of the Fmoc-Phe-Phe-OH solution was poured into the tube and the whole thing was vortexed gently to get a homogeneous pale-pink viscous solution with 1 million/ml cell density. The cell-containing solution was then transferred to a 24 well-plate with 500 μin each well. A further 1 ml of complete culture medium was poured onto each cell-peptide solution drop by drop to get hydrogel formed in seconds.

Figure 7:
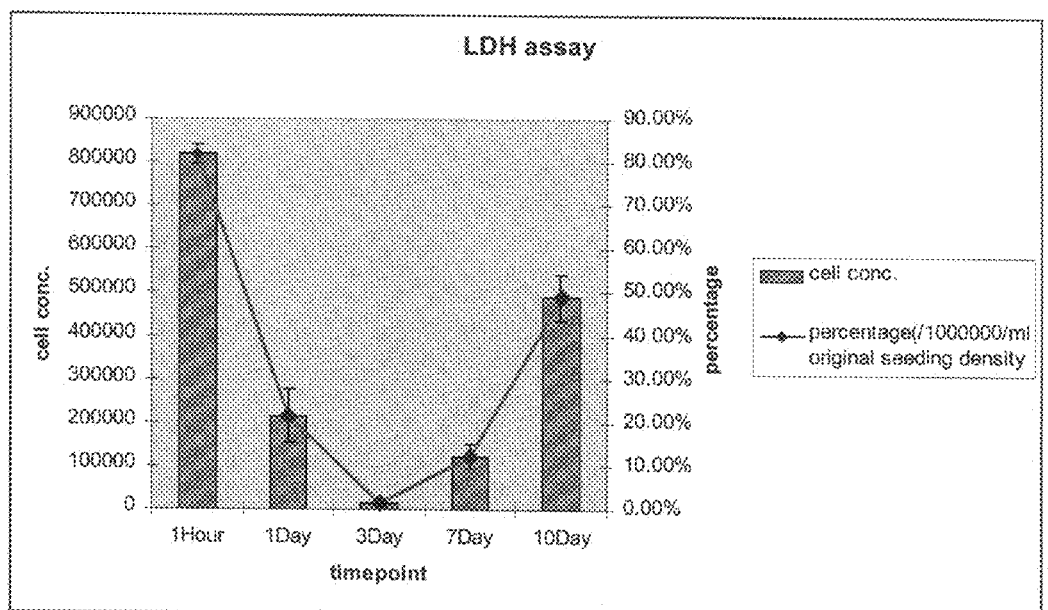
FIG. 7 illustrates the results of the LDH assay (as described in Example 6) of cell viability (3D culture of human adult dermal fibroblasts in Fmoc-Phe-Phe-OH) in accordance with various embodiments of the present invention.

The culture was maintained in a 37° C./5% CO$_2$ incubator for a 10 day period and LDH assay was carried out after 1 hour, 1 day, 3 days, 7 days, and 10 days. The gels were scooped out and vortexed to a viscous liquid mixture and freeze-thawed to release lactate dehydrogenase (LDH) from cells. Assay reagent was then added, the mixture was incubated, and light absorbance at 490 nm was then measured. Absorbance was converted to cell number according to a standard. The results of this LDH assay of cell viability (3D culture of human adult dermal fibroblasts in Fmoc-Phe-Phe-OH) are shown in FIG. 7. The results showed that there was initially a decreasing of cell numbers, but with the remaining living cells, the proliferation happened after 1 week with rapid cell number increasing of 5 folds from day 7 to day 10.

EXAMPLE 7

Fmoc-SEQ. ID. NO. 1-OH (Fmoc-SEQ. ID. NO. 1) adhesion motifs were introduced to tackle the issue of un-spreaded cells in Fmoc-Phe-Phe-OH gels therefore to induce spreading and focal adhesion of dermal fibroblasts in these self-assembled peptide hydrogels. Fmoc-Phe-Phe-OH and Fmoc-Phe-Phe-OH+Fmoc-SEQ. ID. NO. 2-OH (Fmoc-SEQ. ID. NO. 2) combination were set as comparisons.

0.0014 grams of Fmoc-SEQ. ID. NO. 1or Fmoc-SEQ. ID. NO. 2(1 mM/L in later hydrogels), were weighed and mixed with 0.0107 grams Fmoc-Phe-Phe-OH respectively into glass vials, and 0.0107 grams Fmoc-Phe-Phe-OH alone was weighed as well. The above peptide and peptide mixtures were sterilized for 30 minutes by an ultraviolet light exposure with bottles of distilled water, filtered NaOH (Sodium Hydroxide, 0.5 M/L), filtered HCl (Hydrochloric Acid, 0.5 M/L), and relevant apparatus (spatulas, pipettes, Vortex). 2 mL of the sterile distilled water was then added into each glass vial of Fmoc-Phe-Phe-OH, Fmoc-Phe-Phe-OH+Fmoc-SEQ. ID. NO. 1, and Fmoc-Phe-Phe-OH+Fmoc-SEQ. ID. NO. 2, and the mixtures were vortexed for a few seconds to create suspensions. Afterwards, approximately 100 µL of NaOH was gradually pipetted into every suspension (20 µL each pipetting) and the mixtures were further vortexed after every addition of the alkali. The whole mixtures were shaken continually until homogeneous transparent solutions were obtained. The basic peptide solutions (pH around 10) were finally neutralized to pH 7 by dropwise addition of HCl and pH values were monitored by a pH meter with a micro-probe. The solutions were left in a 4° C. refrigerator for overnight until usage.

The solutions were warmed at room temperature on the day of cell culture for about an hour. Human dermal fibroblasts were trypsinised and centrifuged into a loose pellet of 2 million in a centrifuge tube. About 200 µL of complete culture medium (DMEM with 10% bovine fetal serum and 1% antibiotics/antimicotics) was added to the pellet and pipetted to obtain a condensed cell suspension; after which 1800 µL of the Fmoc-Phe-Phe-OH, Fmoc-Phe-Phe-OH+Fmoc-SEQ. ID. NO. 1, or Fmoc-Phe-Phe-OH+Fmoc-SEQ. ID. NO. 2solution was poured into the tube and the whole thing was vortexed gently to get a homogeneous pale-pink viscous solution with 1 million/mL cell density. The cell-containing solutions were then transferred to 24 well-plates separately with 500 µL in each well. A further lmL of complete culture medium was poured onto each cell-peptide solution drop by drop to get hydrogel formed in seconds.

The cell culture in the 3 different gel types were kept in the 37° C./5% $CO_2$ incubator and cell phenotype was observed after 24 hours by an inverted optic microscope.

Figure 8:
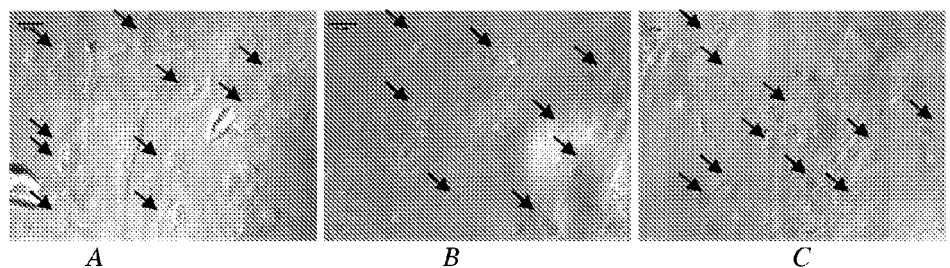
FIG. 8 illustrates the cell phenotype and size comparison (as described in Example 7) in accordance with various embodiments of the present invention. (A): Fmoc-(SEQ. ID. No. 1) +Fmoc-Phe-Phe-OH; (C) Fmoc-(SEQ. ID. NO. 2)+Fmoc-Phe-Phe-OH. The arrows point to the cells.

The results are illustrated in FIG. 8 which shows cell phenotype and size comparison in Fmoc-SEQ. ID. NO. 1+Fmoc-Phe-Phe-OH(A), Fmoc-SEQ. ID. NO. 2+Fmoc-Phe-Phe-OH (C) arrows pointing to cells).

Different from the other two, Fmoc-Phe-Phe-OH+Fmoc-SEQ. ID. NO. 1hydrogels made cells larger with obvious oval to round nucleus and flattened membranes. The average cell size in the RGD-containing hydrogels was 35 microns compared to around 20 microns in the RGE-containing hydrogels or gels without RGE/RGD.

Higher concentrations of RGD/RGE-containing Fmoc-Phe-Phe-OH were prepared with 50% (7.5 mM/L) of Fmoc-SEQ. ID. NO. 1(or Fmoc-SEQ. ID. NO. 2) and 50% of Fmoc-Phe-Phe-OH (7.5 mM/L). Stronger transparent hydrogels were formed as they were easily lifted up with a thin spatula without broken pieces after even 10 days. Same cell-size phenomenon were observed as in 50%:50% (Fmoc-SEQ. ID. NO. 1): Fmoc-Phe-Phe-OH) hydrogels cells were larger with flat membranes compared to those of 50%:50% (Fmoc-SEQ. ID. NO. 2: Fmoc-Phe-Phe-OH) and Fmoc-Phe-Phe-OH hydrogels.

EXAMPLE 8

Human mesenchymal stem cells (MSCs) were isolated from bone marrow taken from patients (with both patient and ethical consent) undergoing hip replacement surgery.A HIS-TOPAQUE (SIGMA-ALDRICH) gradient was used to isolate mononuclear cells and these cells were cultured in monolayer with α-MEM (with 10% heat-inactivated foetal calf serum, 100 U/ml streptomycin/penicillin and 0.85 mM ascorbic acid) under standard culture conditions (humidified atmostphere, 37° C., 5% $CO_2$). After 5 days non-adherent cells were removed by washing with media.

At 80% confluence in passage 3 the MSCs were trypsinised and a cell count was performed. A suitable number of cells were centrifuged at 400 g for 5 minutes and then resuspended in a 10 mM Fmoc-Phe-Phe solution to a final concentration of $4 \times 10^6$ cells/ml. The cell suspension was mixed to ensure even cell distribution and 200 µl layers were pipetted into high pore density (0.4 µm pore size) cell culture inserts in 24-well plates. Media (α-MEM as previously described) was added gently to both the well and the insert and gels were allowed to polymerise.

The cell-seeded gels were then cultured under standard conditions for 14 days with media changed every 2 days. Following culture 1 ml of TRIZOL was added to each insert and the gels disrupted by pipetting. A modified RNA extraction procedure was performed combining both the TRIZOL and PURELINK (INVITROGEN) extraction procedures. RNA was reverse transcribed to cDNA using SUPERSCRIPT II (INVITROGEN) and PCR performed using a standard HOTSTARTAQ (QIAGEN) procedure for the house-keeping gene GAPDH as well as the transcription factor SOX-9, aggrecan and collagen types I and II.

PCR products were run on a 1.5% agarose gel containing ethidium bromide and visualised on a UV-transilluminator.

Figure 9:
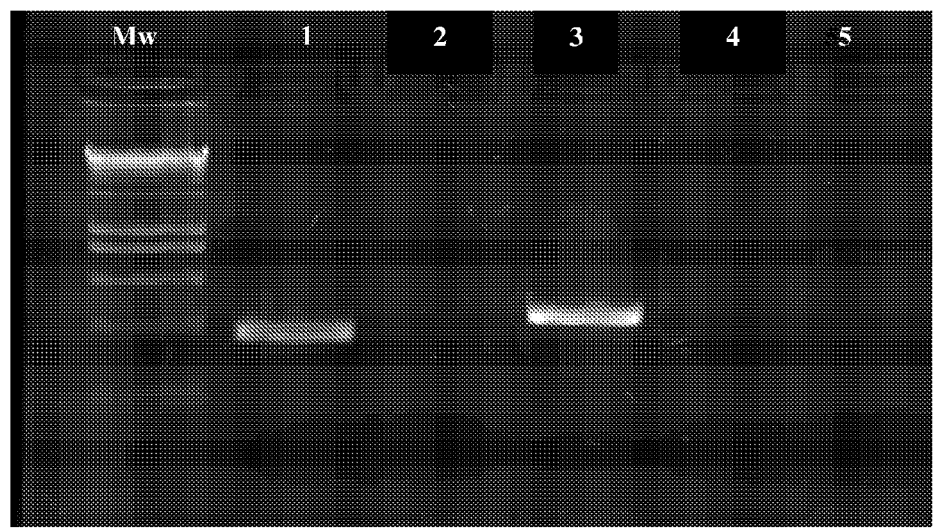
FIG. 9 illustrates the expression of GAPDH and type I collagen by MSCs in Fmoc-F-F gels after 14 days in accordance with various embodiments of the present invention. Agarose gel showing results of PCR on Fmoc-Phe-Phe gels seeded with human MSCs following 14 days in culture is depicted. Mw=molecular weight ladder. Lane 1=GAPDH, lane 2=SOX-9, lane 3=type I collagen, lane 4=type II collagen, lane 5=aggrecan.

The results are shown in FIG. 9. As shown in FIG. 9, expression of GAPDH and type I collagen by MSCs in Fmoc-F-F gels after 14 days showed that there were viable cells present and the lack of expression of SOX-9, type II collagen or aggrecan suggests these cells may be in an undifferentiated state.

EXAMPLE 9

This Example provides a comparison of Fmoc and CBz as aromatic stacking ligands.

In this Example Cryo-SEM was performed using a PHILIPS XL30 ESEM-FG equipped with an OXFORD INSTRUMENT ALTO CT2500 for cryo-transfer and cryo image purposes.

Fmoc-Phe-Phe-OH and Cbz-Phe-Phe-OH where prepared as previously described. Approximately 100 mg of each of the hydrogels prepared at a concentration of 40 mM/L were frozen using liquid nitrogen and then placed in the SEM chamber for sublimation and fracture. The sample specimens were then analysed at various magnifications to observe different characteristics of interest. The images were recorded digitally.

The results in the Cryo-SEM images of FIGS. 10C (Fmoc-Phe-Phe-OH) and 10D (Cbz-Phe-Phe-OH). FIG. 10 shows that gels formed by Fmoc-Phe-Phe-OH and Cbz-Phe-Phe-OH shows slightly different macro-structure but within the dimensions of 5-300 nm similar to that of the extracellular matrix. For the sake of completeness, FIG. 10A shows the structure of Fmoc-Phe-Phe-OH and FIG. 10B shows that of Cbz-Phe-Phe-OH.

Conclusions

As can be seen from the results, the research carried out by the inventors has provided some very promising data. Preliminary analysis of the test samples revealed the possibility of designing stable gels that can withstand cell culture conditions (neutral pH and high ion concentration and 37° C.). These were found to support the proliferation and retention of the phenotype of bovine chondrocytes, human mesenchymal stem cells and human adult dermal fibroblasts.

Hence, the inventors have demonstrated for the first time that short Fmoc-dipeptides and tripeptides cause the self-assembly of a range of fibrous hydrogel scaffolds with different structural and functional properties. These hydrogels are:- (i) stable under tissue culture conditions (high ionic strength, pH 7); (ii) of similar dimensions to fibrous components of the extra cellular matrix (nano-sized fibres); and (iii) capable of supporting cell culture of chondrocytes in 2D and 3D.

The inventors believe that the peptides and the hydrogel cell scaffolds they form may be used in a wide variety of medical applications, such as in wound healing and in tissue regeneration.

---

---

The invention claimed is:

1. A physiologically acceptable hydrogel composition comprising a dispersion phase consisting essentially of an aqueous dispersion phase; and
    a plurality of peptide derivatives, wherein each peptide derivative comprises:
        (a) a peptide consisting of two to six L-amino acid residues, and
        (b) an aromatic stacking ligand, said peptide consisting of two to six amino acids include two adjacent Phe residues,
    wherein the hydrogel is formed by self-assembly of said peptide derivatives in said dispersion phase, and said hydrogel has a pH of 6.5-8.

2. The hydrogel composition as claimed in claim 1 having a pH of about 7.

3. The hydrogel composition as claimed in claim 1 wherein the aromatic stacking ligand is Fmoc.

4. The hydrogel composition as claimed in claim 1 wherein the peptide is a Phe-Phe dipeptide.

5. The hydrogel composition as claimed in claim 1 wherein the peptide includes a Leu-Leu dipeptide.

6. The hydrogel composition as claimed in claim 4 wherein the hydrogel comprises
said peptide derivative comprising
  (a) a peptide consisting of a Phe-Phe dipeptide and
  (b) the aromatic stacking ligand; and
a second peptide derivative comprising
  (a') a peptide consisting of two to six L-amino acid residues and
  (b') an aromatic stacking ligand, wherein said peptide of the second peptide derivative is a Gly-Gly dipeptide.

7. The hydrogel composition as claimed in claim 1 wherein the peptide derivative comprises (a) a peptide consisting of a tripeptide and (b) the aromatic stacking ligand.

8. The hydrogel composition as claimed in claim 7 wherein the tripeptide is Phe-Phe-Phe.

9. The hydrogel composition as claimed in claim 1 wherein the peptide of the peptide derivative has a terminal amino acid residue selected from the group consisting of Phe and Leu, and wherein said aromatic stacking ligand is provided at the opposite end of the peptide.

10. The hydrogel composition as claimed in claim 1 wherein the peptide comprises an Arginine-Glycine-Aspartate (RGD) peptide motif.

11. The hydrogel composition as claimed in claim 10 wherein the or each peptide has the structure A.S.L.-$AA_1$-$AA_2$-RGD, where A.S.L. denotes the Aromatic Stacking Ligand, where AAn denotes amino acid residues in the peptide, and where RGD denotes the RGD motif.

12. The hydrogel composition as claimed in claim 1 wherein at least one peptide in the hydrogel comprises a Lysine-Proline-Valine (KPV) motif.

13. The hydrogel composition as claimed in claim 1 wherein the or each peptide has the structure A.S.L.-$AA_1$-$AA_2$-KPV, where A.S.L. denotes the Aromatic Stacking Ligand, where $AA_n$ denotes amino acid residues in the peptide, and where KPV denotes the KPV motif.

14. The hydrogel composition as claimed in claim 1 wherein the hydrogel incorporates a bioadditive having the structure A.S.L.-K, where the A.S.L. denotes an aromatic stacking ligand, and where the K denotes a lysine residue.

15. The hydrogel composition as claimed in claim 14 comprising a mixture of Fmoc-Phe-Phe as said peptide derivative and Fmoc-Lys as said bioadditive.

16. A method of treating an individual suffering from a medical condition characterised by tissue loss/damage, the method comprising providing at a treatment site of an individual in need of such treatment, a physiologically acceptable hydrogel composition comprising
  a dispersion phase consisting essentially of an aqueous dispersion phase;
  and a plurality of peptide derivatives wherein each peptide derivative comprises:
    (a) a peptide consisting of two to six L-amino acid residues, and
    (b) an aromatic stacking ligand, said peptide of two to six amino acids includes two adjacent Phe residues, wherein the hydrogel is formed by self-assembly of said peptide derivatives in said dispersion phase, and said hydrogel has a pH of 6.5-8.

17. The method as claimed in claim 16 wherein the hydrogel is formed at a pH of between about 6.5 to about 7.5.

18. The method as claimed in claim 16 for the treatment of wounds, related injuries or tissue degenerative disorders.

19. A cell-supporting medium comprising a hydrogel composition as claimed in claim 1 and at least one cell.

20. A method of preparing a cell supporting medium according to claim 19, the method comprising the steps of:
  (i) contacting either a hydrogel as claimed in claim 1, or a precursor composition thereof, with at least one cell; and
  (ii) exposing the hydrogel or composition to conditions such that the at least one cell is supported on and/or in a hydrogel, thereby forming a cell-supporting medium.

21. A method of culturing cells wherein the cells are cultured on or in a hydrogel composition as claimed in claim 1.

22. The method as claimed in claim 21 for use in vitro testing, pharmaceutical screening or as extracellular matrix models.

23. A method of preparing a physiologically acceptable hydrogel composition as claimed in claim 1 comprising the steps of:
  (i) preparing an aqueous solution of said peptide derivatives;
  (ii) setting a pH of said solution to about 9 to 11; and
  (iii) reducing the pH to about 6.5-8 such that a gel formation occurs.

24. The hydrogel composition of claim 1, wherein the hydrogel has a pH of 7-8.

25. The hydrogel composition of claim 1, wherein the hydrogel has a pH of 6.5-7.5.

* * * * *

SEQUENCE LISTING

```
<160> NUMBER OF SEQ ID NOS: 3

<210> SEQ ID NO 1
<211> LENGTH: 5
<212> TYPE: PRT
<213> ORGANISM: Homo sapiens

<400> SEQUENCE: 1

Gly Gly Arg Gly Asp
1               5

<210> SEQ ID NO 2
<211> LENGTH: 5
<212> TYPE: PRT
<213> ORGANISM: Homo sapiens

<400> SEQUENCE: 2

Gly Gly Arg Gly Glu
1               5

<210> SEQ ID NO 3
<211> LENGTH: 5
<212> TYPE: PRT
<213> ORGANISM: Homo sapiens

<400> SEQUENCE: 3

Ile Lys Val Ala Val
1               5
```